United States Patent
Remøy et al.

(10) Patent No.: US 10,709,148 B2
(45) Date of Patent: Jul. 14, 2020

(54) METHOD FOR PRODUCING A PROTEIN PHOSPHOLIPID COMPLEX FROM A CRUSTACEAN CATCH

(71) Applicant: RIMFROST TECHNOLOGIES AS, Fosnavaag (NO)

(72) Inventors: Stig Remøy, Fosnavaag (NO); Inge Bruheim, Volda (NO)

(73) Assignee: Rimfrost Technologies, Fosnavaag (NO)

(*) Notice: Subject to any disclaimer, the term of this patent is extended or adjusted under 35 U.S.C. 154(b) by 0 days.

(21) Appl. No.: 16/206,600

(22) Filed: Nov. 30, 2018

(65) Prior Publication Data

US 2019/0166866 A1   Jun. 6, 2019

Related U.S. Application Data

(60) Provisional application No. 62/594,105, filed on Dec. 4, 2017.

(51) Int. Cl.

| | | |
|---|---|---|
| *A61K 36/00* | (2006.01) | |
| *A23D 9/007* | (2006.01) | |
| *A23L 17/40* | (2016.01) | |
| *C11B 1/10* | (2006.01) | |
| *A23L 33/115* | (2016.01) | |
| *A61K 35/60* | (2006.01) | |
| *A23L 33/18* | (2016.01) | |
| *A23J 3/04* | (2006.01) | |
| *A23J 1/04* | (2006.01) | |
| *A23J 3/34* | (2006.01) | |

(52) U.S. Cl.
CPC ............... *A23D 9/007* (2013.01); *A23J 1/04* (2013.01); *A23J 3/04* (2013.01); *A23J 3/341* (2013.01); *A23L 17/40* (2016.08); *A23L 33/115* (2016.08); *A23L 33/18* (2016.08); *A61K 35/60* (2013.01); *C11B 1/10* (2013.01)

(58) Field of Classification Search
None
See application file for complete search history.

(56) References Cited

U.S. PATENT DOCUMENTS

| | | | |
|---|---|---|---|
| 6,800,299 B1 | 10/2004 | Beaudoin et al. | |
| 8,557,297 B2 | 10/2013 | Bruheim et al. | |
| 8,758,829 B2 | 6/2014 | Jansson et al. | |
| 9,028,877 B2 | 5/2015 | Bruheim et al. | |
| 9,034,388 B2 | 5/2015 | Bruheim et al. | |
| 9,068,142 B2 | 6/2015 | Bruheim et al. | |
| 9,072,752 B1 | 7/2015 | Bruheim et al. | |
| 9,078,905 B2 | 7/2015 | Bruheim et al. | |
| 9,167,832 B2 | 10/2015 | Jansson et al. | |
| 9,320,765 B2 | 4/2016 | Bruheim et al. | |
| 9,375,453 B2 | 6/2016 | Bruheim et al. | |
| 9,480,273 B2 | 11/2016 | Bruheim et al. | |
| 9,644,170 B2 | 5/2017 | Bruheim et al. | |
| 9,738,920 B2 | 8/2017 | Plank | |
| 9,814,256 B2 | 11/2017 | Bruheim et al. | |
| 9,907,321 B2 | 3/2018 | Jasson et al. | |
| 2003/0113432 A1 | 6/2003 | Yoshitomi et al. | |
| 2010/0143571 A1 | 6/2010 | Breivik | |
| 2010/0196538 A1 | 8/2010 | Law | |
| 2012/0149867 A1* | 6/2012 | bruheim et al. | |
| 2018/0168187 A1 | 6/2018 | Jansson et al. | |

FOREIGN PATENT DOCUMENTS

| | | |
|---|---|---|
| WO | 198401715 A1 | 5/1984 |
| WO | 2008060163 A1 | 5/2008 |
| WO | 2010030193 A1 | 3/2010 |
| WO | 2013102792 A2 | 7/2013 |
| WO | 2016190748 A1 | 12/2016 |
| WO | 2018183815 A1 | 10/2018 |

OTHER PUBLICATIONS

Budziński, E., P. Bykowski and D. Dutkiewicz, 1985, Possibilities of processing and marketing of products made from Antarctic krill. FAO Fish. Tech. Pap., (268):46.

Dang, Tem Thi, et al. "Enzyme-assisted peeling of cold water shrimps (Pandalus borealis)." Innovative Food Science & Emerging Technologies 47 (2018): 127-135. Abstract only.

* cited by examiner

*Primary Examiner* — Qiuwen Mi
(74) *Attorney, Agent, or Firm* — Medlen & Carroll, LLP (57) ABSTRACT

A method of producing a protein phospholipid complex from a crustacean catch including protein is claimed where hydrolysis occurs without substantially denaturing the protein from the crustacean catch. A method of producing a stable protein phospholipid emulsion from a crustacean catch is also claimed. A method of producing crustacean oil is claimed where the oil is separated from the hydrolyzed crustacean catch. Other methods of producing a protein phospholipid complex are claimed which relate to not removing the shell, removing the shell, and removing then adding back the shell to form the protein phospholipid complex.

12 Claims, 2 Drawing Sheets

METHOD FOR PRODUCING A PROTEIN PHOSPHOLIPID COMPLEX FROM A CRUSTACEAN CATCH

CROSS-REFERENCE TO RELATED APPLICATION

This application claims the benefit of U.S. Provisional Application Ser. No. 62/594,105, filed on Dec. 4, 2017, which is incorporated herein by reference.

BACKGROUND OF THE INVENTION

In recent years, scientific studies have espoused the health benefits of a diet rich in omega-3 fatty acids such as eicosapentaenoic acid (EPA) and docosahexaenoic acid (DHA). These fatty acid have been shown to be essential for maintaining brain health and studies indicate they also promote cardiovascular health, reduce inflammation and prevent arthritis, improve gastric health, and have anti-depressive effects.

Omega-3 fatty acids occur naturally in various food sources including certain fish, crustaceans, nuts, and seeds. Additionally, concentrated forms of omega-3 fatty acids make up a large segment of the vitamin and supplement industry. Among the animal-derived sources of omega-3 fatty acids, fish oil has gained prominence as being a popular vitamin source. However, fish oil capsules have the drawback of leaving a "fishy" aftertaste.

Scientists are researching alternative sources of omega-3 fatty acids to determine if they may be more bioavailable. For example, some studies have preliminarily shown that krill oil derived from Antarctic hill may be a superior source of omega-3 fatty acids because it is more bioavailable than fish oil. See Ramprasath, et al. "Enhanced increase of omega-3 index in healthy individuals with response to 4-week n-3 fatty acid supplementation from hill oil versus fish oil", Lipids in Health and Disease 2013, 12: 178 and Schuchardt, et al. "Incorporation of EPA and DHA into plasma phospholipids in response to different omega-3 fatty acid formulations—a comparative bioavailability study of fish oil vs. hill oil" Lipids in Health and Disease 2011, 10:145. Some speculate that these omega-3 fatty acids are attached to phospholipids which make them more bioavailable compared to omega-3 fatty acids derived from fish sources which are attached to triglycerides. See Schuchardt, et al. Additionally, hill is sustainable since it is the largest biomass in the world and only less than 1% of hill in the ocean is harvested each year; hill has been marketed as having no aftertaste and non-detectable levels of mercury; and hill contains the antioxidant astaxanthin.

While krill oil seems to be a superior source for omega-3 fatty acids, there remains a need for a better way to process hill in order to harvest the omega-3 fatty acids and produce a product that is bioavailable, low in water and other contaminants, and can be further processed downstream to produce high quality hill oil and other products utilizing the krill protein. More specifically, there is a need for a new method of producing a protein phospholipid complex wherein the digestive enzymes are inactivated by hydrolysis and proteins within the hill are not substantially denatured during the hydrolysis step, and a new method of producing a stable protein phospholipid emulsion where the emulsion does not separate and the water content is low enough to prevent microbiological growth.

SUMMARY OF THE INVENTION

One aspect of the invention relates to a method of producing a protein phospholipid complex (PPC) including the steps of: a) disintegrating a crustacean catch to provide a disintegrated crustacean catch including protein; b) contacting the disintegrated crustacean catch with a proteolytic enzyme to provide a hydrolyzed crustacean catch without substantially denaturing the protein; and c) separating the hydrolyzed crustacean catch to provide a PPC.

In one embodiment, the contacting step includes a second enzyme. Preferably, the second enzyme may include a chitinase, a collagenase, or another proteolytic enzyme. The proteolytic enzyme is preferably a mixture of acid, neutral, and alkaline proteases.

In one embodiment, the proteolytic enzyme in the contacting step includes at least one of a metalloendopeptidase. In another embodiment, the proteolytic enzyme does not include an exopeptidase.

In one embodiment, the contacting step includes contacting with a first protease mixture and a second protease mixture. The first protease mixture having at least one alkaline protease and the second protease mixture having an acid protease, a neutral protease, and an alkaline protease.

Preferably, the first protease mixture includes 0.3-0.5% of the total weight of the disintegrated crustacean catch; and the second protease mixture includes 0.03-0.05% of the total weight of the disintegrated crustacean catch.

In a preferred embodiment, the proteases are from *Bacillus Licheniformis*.

In one embodiment, the contacting step includes contacting with a cell wall degrading enzyme.

Preferably, the disintegrated crustacean catch is contacted with a proteolytic enzyme for over 100 minutes to provide a hydrolyzed crustacean catch. The contacting step may include an organic solvent. The contacting step may include incubating the disintegrated crustacean catch at a temperature range of 45-75° C.

The disintegrated crustacean catch is preferably krill. During the disintegrating step, the crustacean catch may be processed by pulping, milling, grinding, and/or shredding.

The PPC produced by the method may contain a water content less than 15% w/w.

The protein in the krill may include digestive enzymes and other protein (apart from the digestive enzymes).

Another aspect of the invention relates to a method of producing a stable protein phospholipid emulsion including the steps of: a) disintegrating a crustacean catch to provide a disintegrated crustacean catch; b) contacting the disintegrated crustacean catch with a proteolytic enzyme to provide a hydrolyzed crustacean catch; and c) separating the hydrolyzed crustacean catch to provide a stable protein phospholipid emulsion.

In one embodiment, the contacting step includes a second enzyme. Preferably, the second enzyme may include a chitinase, a collagenase, or another proteolytic enzyme. The proteolytic enzyme is preferably a mixture of acid, neutral, and alkaline proteases.

The disintegrated crustacean catch is preferably krill. During the disintegrating step the crustacean catch may be processed by pulping, milling, grinding, and/or shredding.

In one embodiment, the proteolytic enzyme in the contacting step includes at least one metalloendopeptidase. In another embodiment, the proteolytic enzyme does not include an exopeptidase. The contacting step may include an organic solvent.

The contacting step may include incubating the disintegrated crustacean catch at a temperature range of 45-75° C.

The protein phospholipid emulsion produced according to the method may include 45-55% water content v/v.

Another aspect of the invention relates to a stable protein phospholipid emulsion including water, protein, and lipid.

Another aspect of the invention relates to a method of producing crustacean oil including the steps of: a) disintegrating a crustacean catch to provide a disintegrated crustacean catch including protein; b) contacting the disintegrated crustacean catch with a proteolytic enzyme to provide a hydrolyzed crustacean catch without substantially denaturing the protein; and c) separating the hydrolyzed crustacean catch to provide a crustacean oil.

Preferably, the crustacean oil is krill oil and the disintegrated crustacean catch is disintegrated hill. Preferably, the proteolytic enzymes include a mixture of acid, neutral, and alkaline proteases. In one embodiment, the method is performed in the absence of an extraction step.

Another aspect of the invention relates to a nutritional supplement including a crustacean oil and another oil selected from the group consisting of flaxseed oil, pumpkinseed oil, canola oil, soybean oil, walnut oil, fish oil, seal oil, microalgae oil, mussels oil, and shrimp oil. Preferably, the oil is green-lipped mussel oil. Also, the preferred crustacean oil is krill oil.

Another aspect of the invention relates to a method of producing a protein phospholipid complex comprising the steps of a) disintegrating a crustacean catch to provide a disintegrated crustacean catch comprising protein; b) contacting the disintegrated crustacean catch with a proteolytic enzyme to provide a hydrolyzed crustacean catch without denaturing the protein; and c) separating the hydrolyzed crustacean catch to provide a protein phospholipid complex, wherein the shell is not removed from the hydrolyzed crustacean catch during the separating step and is part of the protein phospholipid complex. Preferably, the crustacean catch is hill.

Another aspect of the invention relates to a method of producing a protein phospholipid complex comprising the steps of a) disintegrating a crustacean catch to provide a disintegrated crustacean catch comprising protein; b) contacting the disintegrated crustacean catch with a proteolytic enzyme to provide a hydrolyzed crustacean catch without denaturing the protein; and c) separating the hydrolyzed crustacean catch to provide a protein phospholipid complex comprising the steps of (1) separating shells from the hydrolyzed crustacean catch; (2) pasteurizing the hydrolyzed crustacean catch to inactivate the enzyme; (3) removing excess water by separation; and (4) adding shells back into the hydrolyzed crustacean catch to provide a protein phospholipid complex.

Preferably, the shells are separated from the hydrolyzed crustacean catch in step (1) with a filter or sieve. In another preferred embodiment, the excess water is removed in step (3) by horizontal centrifuge. In step (4), the shells are preferably added back alone or with an insoluble particle for purposes of utility.

An advantage of present invention is that the hydrolysis parameters including the enzymes are selected so that the digestive enzymes are inactivated, i.e., hydrolyzed, while all of the proteins are minimally damaged, i.e., not substantially denatured and available for future use maximizing the value of each catch. Furthermore, partially hydrolyzed proteins can retain more water in a form unavailable for biological growth compared to denatured proteins which means that the PPC may contain a higher level of water which is good for overall processability and storability without an increase in biological activity. Hydrolyzed proteins also are highly digestible and nutritious for aquatic species so by products of the production of hill oil could be incorporated into an aquatic feed.

Another advantage is the preparation of a stable protein phospholipid emulsion that does not separate at elevated temperatures and contains a low water content to prevent microbiological activity and may be beneficial for transport. Both the PPC and stable protein phospholipid emulsion may be further processed so that a high quality crustacean oil may be extracted and the remaining hydrolyzed proteins may also be utilized.

DETAILED DESCRIPTION

Figure 1:
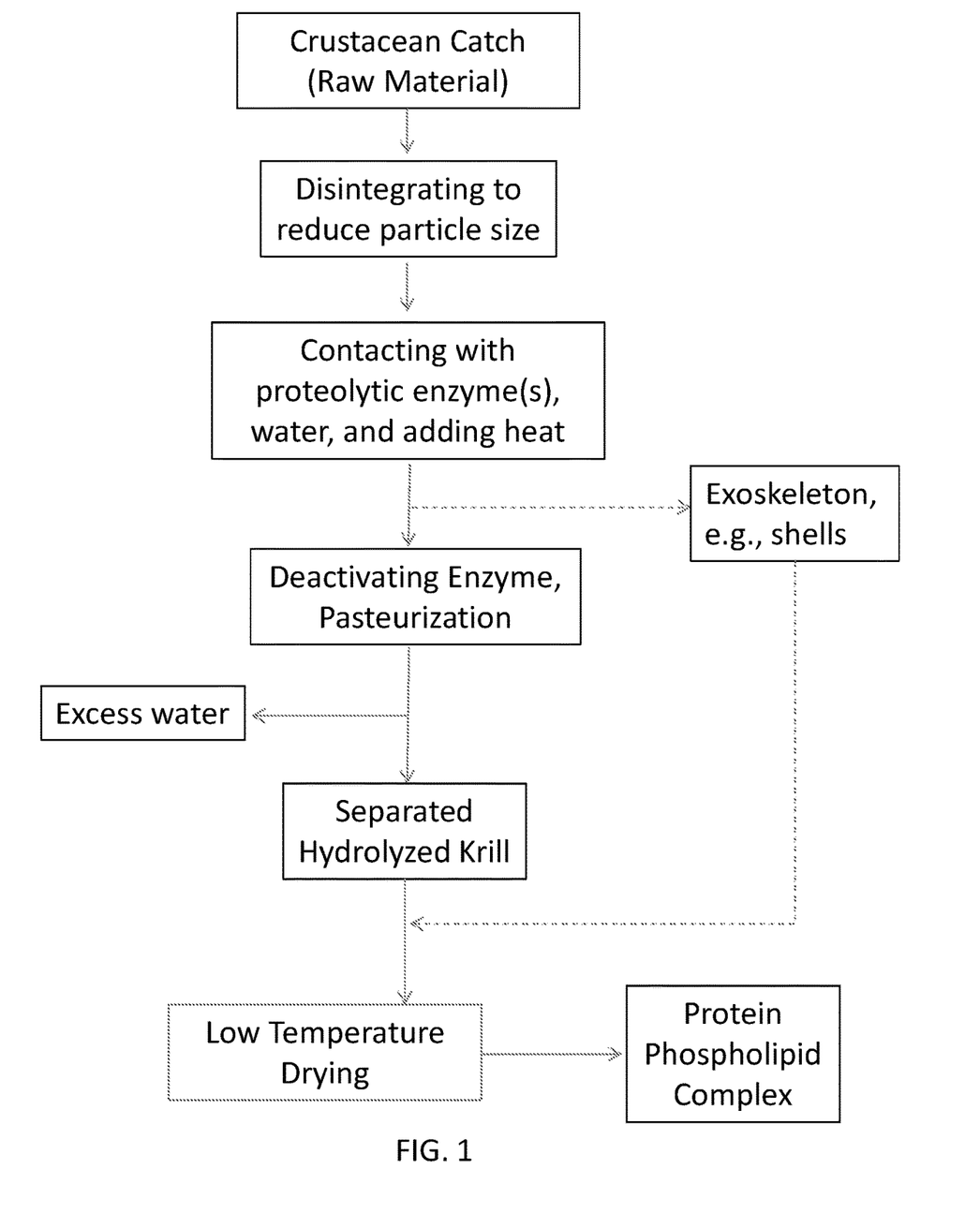
FIG. 1 presents a flow diagram of one embodiment of a method of producing a protein phospholipid complex. In the flow diagram, the dotted lines represent optional steps. For example, the exoskeletons may optionally be removed after the hydrolysis step and optionally added back after the hydrolyzed hill is pasteurized and excess water is removed.
Figure 2:
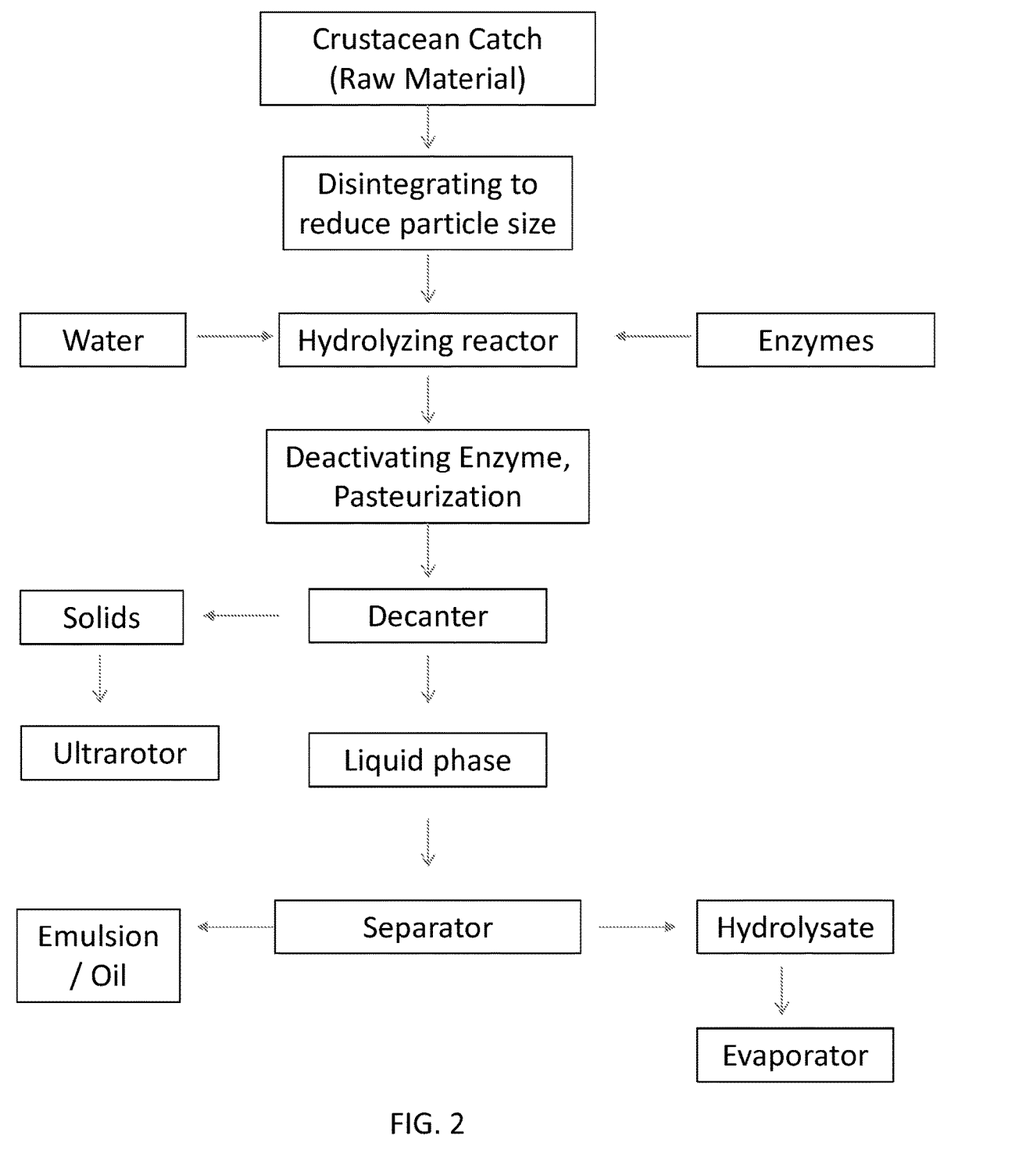
FIG. 2 presents a flow diagram of one embodiment of a method of producing an emulsion or oil.

One aspect of the invention relates to a method of producing a protein phospholipid complex (PPC). In particular, the processing parameters of this method ensure that digestive enzymes naturally present within the hill are inactivated during hydrolysis while maintaining high quality proteins that have not been substantially denatured by the processing conditions associated with hydrolysis.

Crustacean Catch

The first step involves providing a crustacean catch. A crustacean refers to any marine organism having an exoskeleton and is classified as part of the Crustacea subphylum. A crustacean catch includes, but is not limited to, hill, shrimp, lobsters, crab, water fleas, and/or barnacles. The preferred crustacean catch is krill, e.g., Antarctic krill (*Euphausia Superba*). The crustacean catch may be fresh or previously frozen. However, fresh hill caught within 60 minutes, more preferably within 30 minutes is the preferred crustacean catch to process.

Disintegrating Crustacean Catch

The crustacean catch is disintegrated (immediately in the case of freshly caught krill) in order to form a disintegrated crustacean catch. Disintegrating involves mechanically breaking apart the crustacean catch into smaller pieces or smaller particle sizes to be more conducive for subsequent processing steps. The following values may be combined in any manner to create a minima, a maxima, or a range for the particle sizes of the disintegrated crustacean catch: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, and 25 mm.

For example, the disintegrated crustacean catch may have particles sizes of between approximately 1-25 mm, more preferably between approximately 3-15 mm, and most preferably between approximately 3-6 mm.

The crustacean catch may be disintegrated using any conventional means to effectuate a particular range of particle sizes. For example, the disintegration apparatus may grind, pulp, mill, and/or shred the crustacean catch. Examples of disintegration apparatus include, but are not limited to, a knife shredder, a blender, and a homogenizer.

The temperature at which the disintegration process takes place is around the ambient temperature of the water in which the crustacean catch was caught when the crustacean catch is fresh, e.g., hill caught within 60 minutes. Therefore the temperature would be between about −2° C. and about +1° C., preferably about 0° C. to about +6° C.

Hydrolysis

The second step involves contacting the disintegrated crustacean catch with one or more proteolytic enzymes to provide a hydrolyzed crustacean catch. A hydrolyzed crustacean catch is formed when the disintegrated crustacean catch undergoes hydrolysis. Hydrolysis is a chemical reaction or process which can be caused or mediated by a biological agent, such as a proteolytic enzyme, whereby the natural protein sequences become shorter (i.e., for example, by breaking peptide bonds of the amino acid sequence primary structure) to form smaller peptides and free amino acids.

The disintegrated crustacean catch needs to be hydrolyzed so that digestive enzymes such as lipase and phospholipase which are released from the crustacean catch upon death may be inactivated. If these digestive enzymes are not inactivated upon their release, then they will destroy the phospholipids and fatty acids within the crustacean catch. In order to inactivate the digestive enzymes, the disintegrated crustacean catch is contacted with a proteolytic enzyme under certain conditions to form a hydrolyzed crustacean catch. The proteolytic enzyme is chosen specifically to target the digestive enzymes with minimally damaging the other proteins within the krill which may be utilized downstream while separating some phospholipid and peptides from the exoskeletons of the disintegrated crustacean catch.

Conditions of hydrolysis such as choice of enzyme, temperature, pH, and duration are chosen to attain a partially hydrolyzed crustacean catch with a specific degree of hydrolysis. A partially hydrolyzed catch is preferred so the digestive enzymes may be inactivated while other proteins may be broken down into smaller peptides and free amino acids. By contrast, a fully hydrolyzed crustacean catch, which is not preferred, would mean that all of the proteins within the catch would be broken down into free amino acids.

Degree of hydrolysis may be determined by methods known in the art such as pH-stat, trinitrobenzenesulfonic acid (TNBS), o-phthaldialdehyde (OPA), trichloroacetic acid soluble nitrogen (SN-TCA), and formol titration methods. The following percentages may be combined to create a range or be used individually as minima or maxima to specify the degree of hydrolysis 10%, 15%, 20%, 25%, 30%, 35%, 40%, 45%, 50%, 55%, 60%, 65%, 70%, 75%, 80%, 85%, 90%, 95%, 96%, 97%, 98%, and 99%. For example, greater than about 30% of the protein in the crustacean catch is hydrolyzed. More preferably, greater than about 40% of the protein in the crustacean catch is hydrolyzed. In another embodiment, the degree of hydrolysis may be up to 90% to specify that the hydrolysis is almost complete.

Furthermore, partially hydrolyzed proteins by their nature increase digestibility of the proteins. For example, the pepsic digestibility of the partially hydrolyzed proteins may be roughly about 85%, 86%, 87%, 88%, 89%, 90%, 91%, 92%, 93%, 94%, or 95%. Most preferably, the pepsic digestibility of the partially hydrolyzed proteins is about 91%. Increased digestibility means that partially hydrolyzed proteins are nutritious for animals that are unable to synthesize the essential amino acids. There is interest in using the partially hydrolyzed protein by products as a feed supplement for aquatic species and/or pets.

Pepsic digestibility may be measured by standard practices in vivo or by newer practices conducted in vitro. Previously, researchers would determine pepsic digestibility in vivo using rat, rooster, and/or chicken subjects to measure the amount of digested protein when the animal was fed a protein-containing compound. Animal feces would be analyzed for nitrogen-content which would provide an indication of the amount of digestible protein in the product. Newer methods of determining protein digestibility can be conducted in vitro by adding a spectroscopic agent to the hydrolyzed protein solution that reacts with the amine functional group or the carboxylic acid functional group so that the amount of amino acid released during enzymatic digestion may be optically evaluated.

Additionally, the proteolytic enzyme(s), conditions, and duration of hydrolysis are specifically chosen to inactivate the digestive enzymes without substantially denaturing any of the proteins within the krill including the digestive enzymes and other proteins (the proteins apart from the digestive enzymes). Denaturing occurs when the protein loses its quaternary, tertiary, and/or secondary structure which is present in its native state.

In another embodiment, either the digestive enzymes are not denatured or the other proteins are not denatured. Partially hydrolyzed proteins that have not been denatured are preferable because they have been found to retain substantial amounts of water in a form that is unavailable for biological growth up to 2, 3, 4, 5, 6, 7, 8, 9, or 10 times longer than protein that has been denatured which retains less water in a form unavailable for biological growth. The ability to hold water increases the utility of the PPC by increasing flowability and storability of the product. Therefore, it would be advantageous for the PPC or any other downstream product containing the partially hydrolyzed proteins to be able to hold a substantial amount of water without promoting biological growth for a longer period of time.

Without substantially denaturing the other proteins is defined as 0%, less than 1%, less than 2%, less than 3%, less than 4%, less than 5%, less than 6%, less than 7%, less than 8%, less than 9%, less than 10%, less than 20%, less than 25%, or less than 30% denaturing of the other proteins within the hill.

Hydrolysis preferably occurs when the disintegrated crustacean catch is contacted with the proteolytic enzyme and incubated. The optimal temperature of incubation is the temperature to activate the particular enzyme(s) which is conducive for hydrolysis of the digestive enzymes without denaturing the other proteins within the crustacean catch. The temperature can be achieved during processing by any means known in the art. Preferably, the proteolytic enzyme is added to hot water and then mixed with the disintegrated crustacean catch under agitation. Alternatively, the proteolytic enzyme may be added to water and then the mixture may be heated, or the enzyme, water, and disintegrated crustacean catch are mixed together and then heated.

The following percentage values may be combined to create a minima, a maxima, or a range for the amount of water added during the contacting step based upon the weight of the disintegrated catch: 35%, 36%, 37%, 38%, 39%, 40%, 41%, 42%, 43%, 44%, 45%, 46%, 47%, 48%, 49%, 50%, 51%, 52%, 53%, 54%, and 55%. For example, water is added in an amount of up to about 50% of the weight of the disintegrated catch. In another example, about 45% to about 50% of water is added based upon the weight of the disintegrated catch.

The following values may be combined to create a minima and maxima or a range for the temperatures under which the disintegrated crustacean catch is optimally hydrolyzed, i.e., incubated: 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., and 75° C. For example, the contacting step includes incubating the disintegrated crustacean catch at a temperature range of about 45° C. to about 75° C. These temperatures may apply to the temperature of the water or the temperature of the mixture of water, enzyme(s), and/or disintegrated crustacean catch. For example, the water may be heated up to temperatures of about 60° C. before being mixed with the proteolytic enzyme(s). In another example, the enzyme(s) may function optimally at about 45° C. to about 65° C.

The quantity of enzyme used may be determined by a person having ordinary skill in the art to inactivate enough of the digestive enzymes without substantially denaturing the other proteins within the hill and to separate some phospholipid and peptides from the exoskeletons of the disintegrated crustacean catch.

For example, the proteolytic enzyme may be used in a quantity less than about 0.1% of the total weight of the disintegrated crustacean catch. The following values may be combined in any manner to create a range with a minima and a maxima for the quantity of proteolytic enzyme as a percentage of the total weight of the disintegrated crustacean catch: 0.3%, 0.29%, 0.28%, 0.27%, 0.26%, 0.25%, 0.24%, 0.23%, 0.22%, 0.21%, 0.2%, 0.19%, 0.18%, 0.17%, 0.16%, 0.15%, 0.14%, 0.13%, 0.12%, 0.11%, 0.1%, 0.09%, 0.08%, 0.07%, 0.06%, 0.05%, 0.04%, 0.03%, 0.02%, and 0.01%. In one embodiment, the proteolytic enzyme may be used in step b) in a quantity of about 0.01% to 0.1% based upon the total weight of the disintegrated crustacean catch.

The pH of the solution may be adjusted to ensure that hydrolysis proceeds optimally based upon the particular proteolytic enzyme(s) being used.

The hydrolysis step may take any reasonable time to produce a hydrolyzed crustacean catch. Factors affecting the time required for hydrolysis include the temperature and pH of the mixture as well as whether the reaction takes place with or without agitation and the intensity of the agitation.

For example, hydrolysis may take less than 100 minutes. The following values in minutes may be combined in any manner to create a range with a minima and maxima for time necessary for hydrolysis: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40. As an example, hydrolysis may take about 15-18 minutes, or hydrolysis may take less than about 45 minutes.

In another embodiment, hydrolysis may take over 100 minutes. The following values in minutes may be combined in any manner to create a range with a minima and maxima for time necessary for hydrolysis: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, and 240. As an example, hydrolysis may take about 100-180 minutes, or hydrolysis may take less than about 180 minutes.

Proteolytic Enzymes

The proteolytic enzymes useful in the present invention are food grade enzymes that cleave large protein molecules into smaller molecules by hydrolyzing peptide bonds along the protein backbone. As used herein, the term "proteolytic enzyme", "protease", and "peptidase" are used interchangeably. As used herein, the term "exopeptidase" refers to a hydrolase enzyme that removes terminal amino acids of a peptide or protein by cleaving peptide bonds. A terminal amino acid is an amino acid that is within about 10 amino acids of the N-terminus or C-terminus of a protein or peptide. As used herein, the term "endopeptidase" refers to an enzyme that catalyzes the cleavage of peptide bonds within a polypeptide or protein. Peptidase refers to the fact that it acts on peptide bonds and endopeptidase refers to the fact that these are internal bonds.

Proteolytic enzymes include, but are not limited to, esterase enzymes such as carboxylic-ester hydrolases, thioester hydrolases, phosphoric-monoester hydrolases, phosphatases, phosphoric-diester hydrolases, triphosphoric-monoester hydrolases, sulfuric-ester hydrolases, sulfatases, diphosphoric monoesterases, and phosphoric-triester hydrolases; Glycosylases, such as glycosidases, i.e., enzymes that hydrolyse O- and S-glycosyl compounds and those that hydrolyse N-glycosyl compounds; Enzymes that act on ether bonds such as hydrolysing thioether and trialkylsulfonium; peptidases include exopeptidases such as aminopeptidases, dipeptidyl-peptidases and tripeptidyl-peptidases, carboxypeptidases (serine-type carboxypeptidases, metallocarboxypeptidases, cysteine-type carboxypeptidases), dipeptidases, omega peptidases, and peptidyl-dipeptidases, and endopeptidases such as serine endopeptidases, cysteine endopeptidases, aspartic endopeptidases, metalloendopeptidases such as Corolase® 7089 from Ab Enzymes, CAS 9001-92-7, and threonine endopeptidases; enzymes that hydrolyse carbon-halide compounds in a single sub-subclass; enzymes that act on phosphorus-nitrogen bonds; Enzymes that act on sulfur-nitrogen bonds; enzymes that hydrolyse C-phosphono-groups; Enzymes that act on sulfur-sulfur bonds; and enzymes that act on carbon-sulfur bonds.

Examples of each of the above categories of hydrolases are below. Carboxylic-ester hydrolases include carboxylesterase, arylesterase, triacylglycerol lipase, phospholipase A2, lysophospholipase, acetylesterase, acetylcholinesterase, cholinesterase, tropinesterase, pectinesterase, sterol esterase, chlorophyllase, L-arabinonolactonase, gluconolactonase, uronolactonase, tannase, hydroxybutyrate-dimer hydrolase, acylglycerol lipase, 3-oxoadipate enol-lactonase, 1,4-lactonase, galactolipase, 4-pyridoxolactonase, acylcarnitine hydrolase, aminoacyl-tRNA hydrolase, D-arabinonolactonase, 6-phosphogluconolactonase, phospholipase A1, 6-acetylglucose deacetylase, lipoprotein lipase, dihydrocoumarin hydrolase, limonin-D-ring-lactonase, steroid-lactonase, triacetate-lactonase, actinomycin lactonase, orsellinate-depside hydrolase, cephalosporin-C deacetylase, chlorogenate hydrolase, α-amino-acid esterase, 4-methyloxaloacetate esterase, carboxymethylenebutenolidase, deoxylimonate A-ring-lactonase, 1-alkyl-2-acetylglycerophosphocholine esterase, fusarinine-C ornithinesterase, sinapine esterase, wax-ester hydrolase, phorbol-diester hydrolase, phosphatidylinositol deacylase, sialate O-acetylesterase, acetoxybutynylbithiophene deacetylase, acetylsalicylate deacetylase, methylumbelliferyl-acetate deacetylase, 2-pyrone-4,6-dicarboxylate lactonase, N-acetylgalactosaminoglycan deacetylase, juvenile-hormone esterase, bis(2-ethylhexyl)phthalate esterase, protein-glutamate methylesterase, 11-cis-retinyl-palmitate hydrolase, retinoid isomerohydrolase, L-rhamnono-1,4-lactonase, 5-(3,4-diacetoxybut-1-ynyl)-2,2'-bithiophene deacetylase, fatty-acyl-ethyl-ester synthase, xylono-1,4-lactonase, cetraxate benzylesterase, acetylalkylglycerol acetylhydrolase, acetylxylan esterase, feruloyl esterase, cutinase, poly(3-hydroxybutyrate) depolymerase, poly(3-hydroxyoctanoate) depolymerase, acyloxyacyl hydrolase, polyneuridine-aldehyde esterase, hormone-sensitive lipase, acetylajmaline esterase, quorum-quenching N-acyl-homoserine lactonase, pheophorbidase, monoterpene ε-lactone hydrolase, cocaine esterase, pimelyl-[acyl-carrier protein] methyl ester esterase, rhamnogalacturonan acetylesterase, fumonisin B1 esterase, pyrethroid hydrolase, protein phosphatase methylesterase-1, all-trans-retinyl ester 13-cis isomerohydrolase, 2-oxo-3-(5-oxofuran-2-ylidene) propanoate lactonase, 4-sulfomuconolactone hydrolase, mycophenolic acid acyl-glucuronide esterase, versiconal hemiacetal acetate esterase, aclacinomycin methylesterase, D-aminoacyl-tRNA deacylase, methylated diphthine methylhydrolase, [Wnt protein] O-palmitoleoyl-L-serine hydrolase, 6-deoxy-6-sulfogluconolactonase, chlorophyllide a hydrolase, poly(ethylene terephthalate) hydrolase, and mono (ethylene terephthalate) hydrolase.

Thioester hydrolases include acetyl-CoA hydrolase, palmitoyl-CoA hydrolase, succinyl-CoA hydrolase, 3-hydroxyisobutyryl-CoA hydrolase, hydroxymethylglutaryl-CoA hydrolase, hydroxyacylglutathione hydrolase, glutathione thiolesterase, formyl-CoA hydrolase, acetoacetyl-CoA hydrolase, S-formylglutathione hydrolase, S-succinylglutathione hydrolase, oleoyl-[acyl-carrier-protein] hydrolase, citrate-lyase deacetylase, (S)-methylmalonyl-CoA hydrolase, ADP-dependent short-chain-acyl-CoA hydrolase, ADP-dependent medium-chain-acyl-CoA hydrolase, acyl-CoA hydrolase, dodecanoy-[acyl-carrier-protein] hydrolase, palmitoyl[protein] hydrolase, 4-hydroxybenzoyl-CoA thioesterase, phenylacetyl-CoA hydrolase, choloyl-CoA hydrolase, 1,4-dihydroxy-2-naphthoyl-CoA hydrolase, fluoroacetyl-CoA thioesterase, (3S)-malyl-CoA thioesterase, dihydromonacolin L-[lovastatin nonaketide synthase] thioesterase, and 2-aminobenzoylacetyl-CoA thioesterase.

Phosphoric-monoester hydrolases include alkaline phosphatase, acid phosphatase, phosphoserine phosphatase, phosphatidate phosphatase, 5'-nucleotidase, 3'-nucleotidase, 3'(2'),5'-bisphosphate nucleotidase, 3-phytase, glucose-6-phosphatase, glucose-1-phosphatase, fructose-bisphosphatase, trehalose-phosphatase, methylphosphothioglycerate phosphatase, histidinol-phosphatase, protein-serine/threonine phosphatase, [phosphorylase] phosphatase, phosphoglycolate phosphatase, glycerol-2-phosphatase, phosphoglycerate phosphatase, glycerol-1-phosphatase, mannitol-1-phosphatase, sugar-phosphatase, sucrose-phosphate phosphatase, inositol-phosphate phosphatase, 4-phytase, phosphatidylglycerophosphatase, ADP-phosphoglycerate phosphatase, N-acylneuraminate-9-phosphatase, nucleotidase, polynucleotide 3'-phosphatase, polynucleotide 5'-phosphatase, deoxynucleotide 3'-phosphatase, thymidylate 5'-phosphatase, phosphoinositide 5-phosphatase, sedoheptulose-bisphosphatase, 3-phosphoglycerate phosphatase, streptomycin-6-phosphatase, guanidinodeoxy-scyllo-inositol-4-phosphatase, 4-nitrophenylphosphatase, [glycogen-synthase-D] phosphatase, [pyruvate dehydrogenase (acetyl-transferring)]-phosphatase, [acetyl-CoA carboxylase]-phosphatase, 3-deoxy-manno-octulosonate-8-phosphatase, fructose-2,6-bisphosphate 2-phosphatase, [hydroxymethyl-glutaryl-CoA reductase (NADPH)]-phosphatase, protein-tyrosine-phosphatase, [pyruvate kinase]-phosphatase, sorbitol-6-phosphatase, dolichyl-phosphatase, [3-methyl-2-oxobutanoate dehydrogenase (2-methylpropanoyl-transferring)]-phosphatase, [myosin-light-chain] phosphatase, fructose-2,6-bisphosphate 6-phosphatase, caldesmon-phosphatase, inositol-polyphosphate 5-phosphatase, inositol-1,4-bisphosphate 1-phosphatase, sugar-terminal-phosphatase, alkylacetylglycerophosphatase, phosphoenolpyruvate phosphatase, multiple inositol-polyphosphate phosphatase, 2-carboxy-D-arabinitol-1-phosphatase, phosphatidylinositol-3-phosphatase, phosphatidylinositol-3,4-bisphosphate 4-phosphatase, phosphatidylinositol-3,4,5-trisphosphate 3-phosphatase, 2-deoxyglucose-6-phosphatase, glucosylglycerol 3-phosphatase, mannosyl-3-phosphoglycerate phosphatase, 2-phosphosulfolactate phosphatase, 5-phytase, adenosylcobalamin/α-ribazole phosphatase, pyridoxal phosphatase, phosphoethanolamine/phosphocholine phosphatase, lipid-phosphate phosphatase, acireductone synthase, phosphatidylinositol-4,5-bisphosphate 4-phosphatase, mannosylfructose-phosphate phosphatase, 2,3-bisphosphoglycerate 3-phosphatase, diacylglycerol diphosphate phosphatase, D-glycero-β-D-manno-heptose 1,7-bisphosphate 7-phosphatase, D-glycero-α-D-manno-heptose 1,7-bisphosphate 7-phosphatase, ADP-ribose 1"-phosphate phosphatase, glucosyl-3-phosphoglycerate phosphatase, phosphatidylinositol-3,4,5-trisphosphate 5-phosphatase, 2-hydroxy-3-keto-5-methylthiopentenyl-1-phosphate phosphatase, 5"-phosphoribostamycin phosphatase, 5'-deoxynucleotidase, maltose 6'-phosphate phosphatase, 7-methylguanosine nucleotidase, kanosamine-6-phosphate phosphatase, L-galactose 1-phosphate phosphatase, D-galactose 1-phosphate phosphatase, phosphatidylinositol-3,5-bisphosphate 3-phosphatase, pseudouridine 5'-phosphatase, 3',5'-nucleoside bisphosphate phosphatase, IMP-specific 5'-nucleotidase, thiamine phosphate phosphatase, validoxylamine A 7'-phosphate phosphatase, FMN hydrolase, 3-deoxy-D-glycero-D-galacto-nonulopyranosonate 9-phosphatase, 5-amino-6-(5-phospho-D-ribitylamino)uracil phosphatase, and N-acetyl-D-muramate 6-phosphate phosphatase.

Phosphoric-diester hydrolases include phosphodiesterase I, glycerophosphocholine phosphodiesterase, phospholipase C, phospholipase D, phosphoinositide phospholipase C, sphingomyelin phosphodiesterase, serine-ethanolamine-phosphate phosphodiesterase, [acyl-carrier-protein] phosphodiesterase, 2',3'-cyclic-nucleotide 2'-phosphodiesterase, 3',5'-cyclic-nucleotide phosphodiesterase, 3',5'-cyclic-GMP phosphodiesterase, 2',3'-cyclic-nucleotide 3'-phosphodiesterase, glycerophosphocholine cholinephosphodiesterase, alkylglycerophosphoethanolamine phosphodiesterase, CMP-N-acylneuraminate phosphodiesterase, sphingomyelin phosphodiesterase D, glycerol-1,2-cyclic-phosphate 2-phosphodiesterase, glycerophosphoinositol inositolphosphodiesterase, glycerophosphoinositol glycerophosphodiesterase, N-acetylglucosamine-1-phosphodiester α-N-acetylglucosaminidase, glycerophosphodiester phosphodiesterase, dolichylphosphate-glucose phosphodiesterase, dolichyl-phosphate-mannose phosphodiesterase, glycosylphosphatidylinositol phospholipase D, glucose-1-phospho-D-mannosylglycoprotein phosphodiesterase, cyclic-guanylate-specific phosphodiesterase, 3',5'-cyclic-AMP phosphodiesterase, N-acetylphosphatidylethanolamine-hydrolysing phospholipase D, phosphoribosyl 1,2-cyclic phosphate phosphodiesterase, 7,8-dihydroneopterin 2',3'-cyclic phosphate phosphodiesterase, phosphoribosyl 1,2-cyclic phosphate 1,2-diphosphodiesterase, and RNA 2',3'-cyclic 3'-phosphodiesterase.

Triphosphoric-monoester hydrolases include dGTPase.

Sulfuric-ester hydrolases include arylsulfatase, steryl-sulfatase, glycosulfatase, N-acetylgalactosamine-6-sulfatase, choline-sulfatase, cellulose-polysulfatase, cerebroside-sulfatase, chondro-4-sulfatase, chondro-6-sulfatase, disulfoglucosamine-6-sulfatase, N-acetylgalactosamine-4-sulfatase, iduronate-2-sulfatase, N-acetylglucosamine-6-sulfatase, N-sulfoglucosamine-3-sulfatase, monomethyl-sulfatase, D-lactate-2-sulfatase, glucuronate-2-sulfatase, and (R)-specific secondary-alkylsulfatase.

Diphosphoric-monoester hydrolases include prenyl-diphosphatase, guanosine-3',5'-bis(diphosphate) 3'-diphosphatase, monoterpenyl-diphosphatase, geranylgeranyl diphosphate diphosphatase, farnesyl diphosphatase, tuberculosinol synthase, isotuberculosinol synthase, (13E)-labda-7,13-dien-15-ol synthase, geranyl diphosphate diphosphatase, and (+)-kolavelool synthase.

Phosphoric-triester hydrolases include aryldialkylphosphatase and diisopropyl-fluorophosphatase.

Exodeoxyribonucleases producing 5'-phosphomonoesters include exodeoxyribonuclease I, exodeoxyribonuclease III, exodeoxyribonuclease (lambda-induced), exodeoxyribonuclease (phage SP3-induced), exodeoxyribonuclease V, exodeoxyribonuclease VII, adenosine-5'-diphospho-5'-[DNA] diphosphatase, and guanosine-5'-diphospho-5'-[DNA] diphosphatase.

Exodeoxyribonucleases producing 3'-phosphomonoesters include 5' to 3' exodeoxyribonuclease (nucleoside 3'-phosphate-forming) and DNA-3'-diphospho-5'-guanosine diphosphatase.

Exoribonucleases producing 5'-phosphomonoesters include exoribonuclease II, exoribonuclease H, oligonucleotidase, poly(A)-specific ribonuclease, and ribonuclease D.

Exoribonucleases producing 3'-phosphomonoesters include yeast ribonuclease.

Exonucleases that are active with either ribo- or deoxyribonucleic acids and produce 5'-phosphomonoesters include venom exonuclease.

Exonucleases that are active with either ribo- or deoxyribonucleic acids and produce 3'-phosphomonoesters such as spleen exonuclease;

Endodeoxyribonucleases producing 5'-phosphomonoesters include deoxyribonuclease I, deoxyribonuclease IV, type I site-specific deoxyribonuclease, type II site-specific deoxyribonuclease, type III site-specific deoxyribonuclease, CC-preferring endodeoxyribonuclease, deoxyribonuclease V, T$_4$ deoxyribonuclease II, and T$_4$ deoxyribonuclease IV.

Endodeoxyribonucleases producing 3'-phosphomonoesters include deoxyribonuclease II.

*Aspergillus* deoxyribonuclease K1 include crossover junction endodeoxyribonuclease and deoxyribonuclease X.

Site-specific endodeoxyribonucleases that are specific for altered bases include deoxyribonuclease (pyrimidine dimer).

Endoribonucleases producing 5'-phosphomonoesters are also included.

*Physarum polycephalum* ribonuclease include ribonuclease α, ribonuclease III, ribonuclease H, ribonuclease P, ribonuclease IV, ribonuclease P4, ribonuclease M5, ribonuclease [poly-(U)-specific], ribonuclease IX, tRNase Z, ribonuclease E, and retroviral ribonuclease H; Endoribonucleases producing 3'-phosphomonoesters such as ribonuclease T$_2$.

*Bacillus subtilis* ribonuclease include ribonuclease T$_1$, ribonuclease U$_2$, and pancreatic ribonuclease.

*Enterobacter* ribonuclease include ribonuclease F, ribonuclease V, and rRNA endonuclease.

Endoribonucleases that are active with either ribo- or deoxyribonucleic acids and produce 5'-phosphomonoesters; *Aspergillus* nuclease S1; and *Serratia marcescens* nuclease are also included.

Endoribonucleases that are active with either ribo- or deoxyribonucleic acids and produce 3'-phosphomonoesters include micrococcal nuclease.

Glycosylases are also included.

Glycosidases, i.e. enzymes that hydrolyse O- and S-glycosyl compounds include α-amylase, β-amylase, glucan 1,4-α-glucosidase, cellulose, endo-1,3(4)-β-glucanase, inulinase, endo-1,4-β-xylanase, oligo-1,6-glucosidase, dextranase, chitinase, polygalacturonase, lysozyme, exo-α-sialidase, α-glucosidase, β-glucosidase, α-galactosidase, β-galactosidase, α-mannosidase, β-mannosidase, β-fructofuranosidase, α,α-trehalase, β-glucuronidase, endo-1,3-β-xylanase, amylo-α-1,6-glucosidase, hyaluronoglucosaminidase, hyaluronoglucuronidase, xylan 1,4β-xylosidase, β-D-fucosidase, glucan endo-1,3-β-D-glucosidase, α-L-rhamnosidase, pullulanase, GDP-glucosidase, β-L-rhamnosidase, fucoidanase, glucosylceramidase, galactosylceramidase, galactosylgalactosylglucosylceramidase, sucrose α-glucosidase, α-N-acetylgalactosaminidase, α-N-acetylglucosaminidase, α-L-fucosidase, β-N-acetylhexosaminidase, β-N-acetylgalactosaminidase, cyclomaltodextrinase, non-reducing end α-L-arabinofuranosidase, glucuronosyl-disulfoglucosamine glucuronidase, isopullulanase, glucan 1,3-β-glucosidase, glucan endo-1,3-α-glucosidase, glucan 1,4-α-maltotetraohydrolase, mycodextranase, glycosylceramidase, 1,2-α-L-fucosidase, 2,6β-fructan 6-levanbiohydrolase, levanase, quercitrinase, galacturan 1,4-α-galacturonidase, isoamylase, glucan 1,6-α-glucosidase, glucan endo-1,2-β-glucosidase, xylan 1,3β-xylosidase, licheninase, glucan 1,4-β-glucosidase, glucan endo-1,6-β-glucosidase, L-iduronidase, mannan 1,2-(1,3)-α-mannosidase, mannan endo-1,4-β-mannosidase, fructan β-fructosidase, β-agarase, exo-poly-α-galacturonosidase, κ-carrageenase, glucan 1,3-α-glucosidase, 6-phospho-β-galactosidase, 6-phospho-β-glucosidase, capsular-polysaccharide endo-1,3-α-galactosidase, non-reducing end β-L-arabinopyranosidase, arabinogalactan endo-β-1,4-galactanase, cellulose 1,4β-cellobiosidase (non-reducing end), peptidoglycan β-N-acetylmuramidase, α,α-phosphotrehalase, glucan 1,6-α-isomaltosidase, dextran 1,6-α-isomaltotriosidase, mannosyl-glycoprotein endo-β-N-acetylglucosaminidase, endo-α-N-acetylgalactosaminidase, glucan 1,4-α-maltohexaosidase, arabinan endo-1,5-α-L-arabinanase, mannan 1,4-mannobiosidase, mannan endo-1,6-α-mannosidase, blood-group-substance endo-1,4-β-galactosidase, keratan-sulfate endo-1,4-β-galactosidase, steryl-β-glucosidase, 3a(S)-strictosidine β-glucosidase, mannosyl-oligosaccharide glucosidase, protein-glucosylgalactosylhydroxylysine glucosidase, lactase, endogalactosaminidase, 1,3-α-L-fucosidase, 2-deoxyglucosidase, mannosyl-oligosaccharide 1,2-α-mannosidase, mannosyl-oligosaccharide 1,3-1,6-α-mannosidase, branched-dextran exo-1,2-α-glucosidase, glucan 1,4-α-maltotriohydrolase, amygdalin β-glucosidase, prunasin β-glucosidase, vicianin β-glucosidase, oligoxyloglucan β-glycosidase, polymannuronate hydrolase, maltose-6'-phosphate glucosidase, endoglycosylceramidase, 3-deoxy-2-octulosonidase, raucaffricine β-glucosidase, coniferin 13-glucosidase, 1,6-α-L-fucosidase, glycyrrhizin hydrolase, endo-α-sialidase, glycoprotein endo-α-1,2-mannosidase, xylan α-1,2-glucuronosidase, chitosanase, glucan 1,4-α-maltohydrolase, difructose-anhydride synthase, neopullulanase, glucuronoarabinoxylan endo-1,4-β-xylanase, mannan exo-1,2-1,6-α-mannosidase, α-glucuronidase, lacto-N-biosidase, 4-α-D-{(1→4)-α-D-glucano}trehalose trehalohydrolase, limit dextrinase, poly(ADP-ribose) glycohydrolase, 3-deoxyoctulosonase, galactan 1,3-β-galactosidase, β-galactofuranosidase, thioglucosidase, 13-primeverosidase, oligoxyloglucan reducing-end-specific cellobiohydrolase, xyloglucan-specific endo-β-1,4-glucanase, mannosylglycoprotein endo-β-mannosidase, fructan β-(2,1)-fructosidase, fructan β-(2,6)-fructosidase, xyloglucan-specific exo-β-1,4-glucanase, oligosaccharide reducing-end xylanase, ι-carrageenase, α-agarase, α-neoagaro-oligosaccharide hydrolase, β-apiosyl-β-glucosidase, λ-carrageenase, 1,6-α-D-mannosidase, galactan endo-1,6β-galactosidase, exo-1,4-β-D-glucosaminidase, heparanase, baicalin-β-D-glucuronidase, hesperidin 6-O-α-L-rhamnosyl-β-D-glucosidase, protein O-GlcNAcase, mannosylglycerate hydrolase, rhamnogalacturonan hydrolase, unsaturated rhamnogalacturonyl hydrolase, rhamnogalacturonan galacturonohydrolase, rhamnogalacturonan rhamnohydrolase, β-D-glucopyranosyl abscisate β-glucosidase, cellulose 1,4-β-cellobiosidase (reducing end), α-D-xyloside xylohydrolase, β-porphyranase, gellan tetrasaccharide unsaturated glucuronosyl hydrolase, unsaturated chondroitin disaccharide hydrolase, galactan endo-β-1,3-galactanase, 4-hydroxy-7-methoxy-3-oxo-3,4-dihydro-2H-1,4-benzoxazin-2-yl glucoside β-D-glucosidase, UDP-N-acetylglucosamine 2-epimerase (hydrolysing), UDP-N,N'-diacetylbacillosamine 2-epimerase (hydrolysing), non-reducing end β-L-arabinofuranosidase, protodioscin 26-O-β-D-glucosidase, (Ara-f)3-Hyp β-L-arabinobiosidase, avenacosidase, dioscin glycosidase (diosgenin-forming), dioscin glycosidase (3-O-β-D-Glc-diosgenin-forming), ginsenosidase type III, ginsenoside Rb1 β-glucosidase, ginsenosidase type I, ginsenosidase type IV, 20-O-multi-glycoside ginsenosidase, limit dextrin α-1,6-maltotetraose-hydrolase, β-1,2-mannosidase, α-mannan endo-1,2-α-mannanase, sulfoquinovosidase, exo-chitinase (non-reducing end), exo-chitinase (reducing end), endo-chitodextinase, carboxymethylcellulase, 1,3-α-isomaltosidase, and isomaltose glucohydrolase.

Hydrolysing N-glycosyl compounds include purine nucleosidase, inosine nucleosidase, uridine nucleosidase, AMP nucleosidase, NAD+ glycohydrolase, ADP-ribosyl cyclase/cyclic ADP-ribose hydrolase, adenosine nucleosidase, ribosylpyrimidine nucleosidase, adenosylhomocysteine nucleosidase, pyrimidine-5'-nucleotide nucleosidase, β-aspartyl-N-acetylglucosaminidase, inosinate nucleosidase, 1-methyladenosine nucleosidase, NMN nucleosidase, DNA-deoxyinosine glycosylase, methylthioadenosine nucleosidase, deoxyribodipyrimidine endonucleosidase, [protein ADP-ribosylarginine] hydrolase, DNA-3-methyladenine glycosylase I, DNA-3-methyladenine glycosylase II, rRNA N-glycosylase, DNA-formamidopyrimidine glycosylase, ADP-ribosyl-[dinitrogen reductase] hydrolase, N-methyl nucleosidase, futalosine hydrolase, uracil-DNA glycosylase, double-stranded uracil-DNA glycosylase, thymine-DNA glycosylase, and aminodeoxyfutalosine nucleosidase.

Thioether and trialkylsulfonium hydrolases include adenosylhomocysteinase and adenosylmethionine hydrolase.

Ether hydrolases include isochorismatase, lysoplasmalogenase, trans-epoxysuccinate hydrolase, leukotriene-A4 hydrolase, hepoxilin-epoxide hydrolase, limonene-1,2-epoxide hydrolase, microsomal epoxide hydrolase, soluble epoxide hydrolase, cholesterol-5,6-oxide hydrolase, oxepin-CoA hydrolase, chorismatase, 2,4-dinitroanisole O-demethylase, and trans-2,3-dihydro-3-hydroxyanthranilic acid synthase.

Aminopeptidases include leucyl aminopeptidase, membrane alanyl aminopeptidase, cystinyl aminopeptidase, tripeptide aminopeptidase, prolyl aminopeptidase, aminopeptidase B, glutamyl aminopeptidase, Xaa-Pro aminopeptidase, bacterial leucyl aminopeptidase, clostridial aminopeptidase, cytosol alanyl aminopeptidase, aminopeptidase Y, Xaa-Trp aminopeptidase, tryptophanyl aminopeptidase, methionyl aminopeptidase, D-stereospecific aminopeptidase, aminopeptidase Ey, aspartyl aminopeptidase, aminopeptidase I, PepB aminopeptidase, aminopeptidase S, Xaa-His dipeptidase, Xaa-Arg dipeptidase, Xaa-methyl-His dipeptidase, Glu-Glu dipeptidase, Xaa-Pro dipeptidase, Met-Xaa dipeptidase, non-stereospecific dipeptidase, cytosol nonspecific dipeptidase, membrane dipeptidase, b-Ala-His dipeptidase, dipeptidase E, and D-Ala-D-Ala dipeptidase.

Dipeptidyl-peptidases and tripeptidyl-peptidases include dipeptidyl-peptidase I, dipeptidyl-peptidase II, dipeptidyl-peptidase III, dipeptidyl-peptidase IV, dipeptidyl-dipeptidase, tripeptidyl-peptidase I, tripeptidyl-peptidase II, Xaa-Pro dipeptidyl-peptidase, and Xaa-Xaa-Pro tripeptidyl-peptidase, Peptidyl-dipeptidases such as peptidyl-dipeptidase A, peptidyl-dipeptidase B, peptidyl-dipeptidase Dcp, and cyanophycinase, Serine-type carboxypeptidases such as lysosomal Pro-Xaa carboxypeptidase, serine-type D-Ala-D-Ala carboxypeptidase, carboxypeptidase C, and carboxypeptidase D, Metallocarboxypeptidases such as carboxypeptidase A, carboxypeptidase B, lysine carboxypeptidase, Gly-Xaa carboxypeptidase, alanine carboxypeptidase, muramoylpentapeptide carboxypeptidase, carboxypeptidase E, glutamate carboxypeptidase, carboxypeptidase M, muramoyltetrapeptide carboxypeptidase, zinc D-Ala-D-Ala carboxypeptidase, carboxypeptidase A2, membrane Pro-Xaa carboxypeptidase, tubulinyl-Tyr carboxypeptidase, carboxypeptidase T, carboxypeptidase Taq, carboxypeptidase U, glutamate carboxypeptidase II, metallocarboxypeptidase D, and angiotensin-converting enzyme 2.

Cysteine-type carboxypeptidases include cathepsin X.

Omega peptidases include acylaminoacyl-peptidase, peptidyl-glycinamidase, pyroglutamyl-peptidase I, b-aspartyl-peptidase, pyroglutamyl-peptidase II, N-formylmethionyl-peptidase, g-glutamyl hydrolase, g-D-glutamyl-meso-diaminopimelate peptidase, and ubiquitinyl hydrolase 1.

Serine endopeptidases include Chymotrypsin, chymotrypsin C, metridin, trypsin, thrombin, coagulation factor Xa, plasmin, enteropeptidase, acrosin, α-lytic endopeptidase, glutamyl endopeptidase, cathepsin G, coagulation factor VIIa, coagulation factor IXa, cucumisin, prolyl oligopeptidase, coagulation factor Xia, brachyuran, plasma kallikrein, tissue kallikrein, pancreatic elastase, leukocyte elastase, coagulation factor XIIa, chymase, complement subcomponent Clr, complement subcomponent Cls, classical-complement-pathway C3/C5 convertase, complement factor I, complement factor D, alternative-complement-pathway C3/C5 convertase, cerevisin, hypodermin C, lysyl endopeptidase, endopeptidase La, g-renin, venombin AB, leucyl endopeptidase, tryptase, scutelarin, kexin, subtilisin, oryzin, peptidase K, thermomycolin, thermitase, endopeptidase So, t-plasminogen activator, protein C (activated), pancreatic endopeptidase E, pancreatic elastase II, IgA-specific serine endopeptidase, u-plasminogen activator, venombin A, furin, myeloblastin, semenogelase, granzyme A, granzyme B, streptogrisin A, streptogrisin B, glutamyl endopeptidase II, oligopeptidase B, limulus clotting factor C, limulus clotting factor B, limulus clotting enzyme, repressor LexA, signal peptidase I, togavirin, flavivirin, endopeptidase Clp, proprotein convertase 1, proprotein convertase 2, snake venom factor V activator, lactocepin, assemblin, hepacivirin, spermosin, sedolisin, xanthomonalisin, C-terminal processing peptidase, physarolisin, mannan-binding lectin-associated serine protease-2, rhomboid protease, hepsin, peptidase Do, HtrA2 peptidase, Matriptase, C5a peptidase, aqualysin 1, site-1 protease, pestivirus NS3 polyprotein peptidase, equine arterivirus serine peptidase, infectious pancreatic necrosis birnavirus Vp4 peptidase, SpoIVB peptidase, stratum corneum chymotryptic enzyme, kallikrein 8, kallikrein 13, and oviductin.

Cysteine endopeptidases include cathepsin B, papain, ficain, chymopapain, asclepain, clostripain, streptopain, actinidain, cathepsin L, cathepsin H, cathepsin T, glycyl endopeptidase, cancer procoagulant, cathepsin S, picornain 3C, picornain 2A, caricain, ananain, stem bromelain, fruit bromelain, legumain, histolysain, caspase-1, gingipain R, cathepsin K, adenain, bleomycin hydrolase, cathepsin F, cathepsin O, cathepsin V, nuclear-inclusion-a endopeptidase, helper-component proteinase, L-peptidase, gingipain K, staphopain, separase, V-cath endopeptidase, cruzipain, calpain-1, calpain-2, calpain-3, caspase-2, caspase-3, caspase-4, caspase-5, caspase-6, caspase-7, caspase-8, caspase-9, caspase-10, caspase-11, peptidase 1 (mite), calicivirin, zingipain, Ulpl peptidase, SARS coronavirus main proteinase, sortase A, and sortase B.

Aspartic endopeptidases include pepsin A, pepsin B, gastricsin, chymosin, cathepsin D, nepenthesin, renin, HIV-1 retropepsin, pro-opiomelanocortin converting enzyme, aspergillopepsin I, aspergillopepsin II, penicillopepsin, rhizopuspepsin, endothiapepsin, mucorpepsin, candidapepsin, saccharopepsin, rhodotorulapepsin, acrocylindropepsin, polyporopepsin, pycnoporopepsin, scytalidopepsin A, scytalidopepsin B, cathepsin E, barrierpepsin, signal peptidase II, plasmepsin I, plasmepsin II, phytepsin, yapsin 1, thermopsin, prepilin peptidase, nodavirus endopeptidase, memapsin 1, memapsin 2, HIV-2 retropepsin, plasminogen activator Pla, omptin, human endogenous retrovirus K endopeptidase, HycI peptidase.

Metalloendopeptidases include atrolysin A, microbial collagenase, leucolysin, interstitial collagenase, neprilysin, envelysin, IgA-specific metalloendopeptidase, procollagen N-endopeptidase, thimet oligopeptidase, neurolysin, stromelysin 1, meprin A, procollagen C-endopeptidase, peptidyl-Lys metalloendopeptidase, astacin, stromelysin 2, matrilysin, gelatinase A, vibriolysin, pseudolysin, thermolysin, bacillolysin, aureolysin, coccolysin, mycolysin, b-lytic metalloendopeptidase, peptidyl-Asp metalloendopeptidase, neutrophil collagenase, gelatinase B, leishmanolysin, saccharolysin, gametolysin, deuterolysin, serralysin, atrolysin B, atrolysin C, atroxase, atrolysin F, adamalysin, horrilysin, ruberlysin, bothropasin, bothrolysin, ophiolysin, trimerelysin I, trimerelysin II, mucrolysin, pitrilysin, insulysin, O-sialoglycoprotein endopeptidase, russellysin, mitochondrial intermediate peptidase, dactylysin, nardilysin, magnolysin, meprin B, mitochondrial processing peptidase, macrophage elastase, choriolysin L, choriolysin H, tentoxilysin, bontoxilysin, oligopeptidase A, endothelin-converting enzyme 1, fibrolase, jararhagin, fragilysin, lysostaphin, flavastacin, snapalysin, gpr endopeptidase, pappalysin-1, membrane-type matrix metalloproteinase-1, ADAM10 endopeptidase, ADAMTS-4 endopeptidase, anthrax lethal factor endopeptidase, Ste24 endopeptidase, S2P endopeptidase, ADAM 17 endopeptidase, and ADAMTS13 endopeptidase.

Threonine endopeptidases include proteasome endopeptidase complex and HslU-HslV peptidase.

Endopeptidases of unknown catalytic mechanism are also included.

Acting on carbon-nitrogen bonds, other than peptide bonds, in linear amides include asparaginase, glutaminase, ω-amidase, amidase, urease, β-ureidopropionase, ureidosuccinase, formylaspartate deformylase, arylformamidase, formyltetrahydrofolate deformylase, penicillin amidase, biotinidase, aryl-acylamidase, N-acyl-aliphatic-L-amino acid amidohydrolase, aspartoacylase, acetylornithine deacetylase, acyl-lysine deacylase, succinyl-diaminopimelate desuccinylase, nicotinamidase, citrullinase, N-acetyl-β-alanine deacetylase, pantothenase, ceramidase, choloylglycine hydrolase, N-acetylglucosamine-6-phosphate deacetylase, N4-(β-N-acetylglucosaminyl)-L-asparaginase, N-acetylmuramoyl-L-alanine amidase, 2-(acetamidomethylene)succinate hydrolase, 5-aminopentanamidase, formylmethionine deformylase, hippurate hydrolase, N-acetylglucosamine deacetylase, D-glutaminase, N-methyl-2-oxoglutaramate hydrolase, glutamin-(asparagin-)ase, alkylamidase, acylagmatine amidase, chitin deacetylase, nicotinamide-nucleotide amidase, peptidyl-glutaminase, protein-glutamine glutaminase, 6-aminohexanoate-oligomer exohydrolase, N-acetyldiaminopimelate deacetylase, acetylspermidine deacetylase, formamidase, pentanamidase, 4-acetamidobutyryl-CoA deacetylase, peptide-N4-(N-acetyl-β-glucosaminyl)asparagine amidase, N-carbamoylputrescine amidase, allophanate hydrolase, long-chain-fatty-acyl-glutamate deacylase, N,N-dimethylformamidase, tryptophanamidase, N-benzyloxycarbonylglycine hydrolase, N-carbamoylsarcosine amidase, N-(long-chain-acyl)ethanolamine deacylase, mimosinase, acetylputrescine deacetylase, 4-acetamidobutyrate deacetylase, Na-benzyloxycarbonylleucine hydrolase, theanine hydrolase, 2-(hydroxymethyl)-3-(acetamidomethylene)succinate hydrolase, 4-methyleneglutaminase, N-formylglutamate deformylase, glycosphingolipid deacylase, aculeacin-A deacylase, N-feruloylglycine deacylase, D-benzoylarginine-4-nitroanilide amidase, carnitinamidase, chenodeoxycholoyltaurine hydrolase, urethanase, arylalkyl acylamidase, N-carbamoyl-D-amino-acid hydrolase, glutathionylspermidine amidase, phthalyl amidase, N-acyl-D-amino-acid deacylase, N-acyl-D-glutamate deacylase, N-acyl-D-aspartate deacylase, biuret amidohydrolase, (S)—N-acetyl-1-phenylethylamine hydrolase, mandelamide amidase, N-carbamoyl-L-amino-acid hydrolase, peptide deformylase, N-acetylglucosaminylphosphatidylinositol deacetylase, adenosylcobinamide hydrolase, N-substituted formamide deformylase, pantetheine hydrolase, glutaryl-7-aminocephalosporanic-acid acylase, γ-glutamyl-γ-aminobutyrate hydrolase, N-malonylurea hydrolase, succinylglutamate desuccinylase, acyl-homoserine-lactone acylase, histone deacetylase, fatty acid amide hydrolase, (R)-amidase, L-proline amide hydrolase, 2-amino-5-formylamino-6-ribosylaminopyrimidin-4(3H)-one 5'-monophosphate deformylase, N-acetyl-1-D-myo-inositol-2-amino-2-deoxy-α-D-glucopyranoside deacetylase, peptidoglycan-N-acetylglucosamine deacetylase, chitin disaccharide deacetylase, N-formylmaleamate deformylase, maleamate amidohydrolase, UDP-3-O-acyl-N-acetylglucosamine deacetylase, sphingomyelin deacylase, peroxyureidoacrylate/ureidoacrylate amidohydrolase, 2-oxoglutaramate amidase, 2'-N-acetylparomamine deacetylase, 2'''-acetyl-6'''-hydroxyneomycin C deacetylase, N-acyl-aromatic-L-amino acid amidohydrolase, mycothiol S-conjugate amidase, ureidoglycolate amidohydrolase, 6-aminohexanoate-oligomer endohydrolase, γ-glutamyl hercynylcysteine S-oxide hydrolase, Pup amidohydrolase, protein N-terminal asparagine amidohydrolase, protein N-terminal glutamine amidohydrolase, γ-glutamylanilide hydrolase, protein deglycase, N2-acetyl-L-2,4-diaminobutanoate deacetylase, oxamate amidohydrolase, and jasmonoyl-L-amino acid hydrolase.

In cyclic amides include barbiturase, dihydropyrimidinase, dihydroorotase, carboxymethylhydantoinase, allantoinase, β-lactamase, imidazolonepropionase, 5-oxoprolinase (ATP-hydrolysing), creatininase, L-lysine-lactamase, 6-aminohexanoate-cyclic-dimer hydrolase, 2,5-dioxopiperazine hydrolase, N-methylhydantoinase (ATP-hydrolysing), cyanuric acid amidohydrolase, maleimide hydrolase, hydroxyisourate hydrolase, enamidase, streptothricin hydrolase, and isatin hydrolase.

In linear amidines include arginase, guanidinoacetase, creatinase, allantoicase, formimidoylaspartate deiminase, arginine deiminase, guanidinobutyrase, formimidoylglutamase, allantoate deiminase, D-arginase, agmatinase, agmatine deiminase, formimidoylglutamate deiminase, amidinoaspartase, protein-arginine deiminase, methylguanidinase, guanidinopropionase, dimethylargininase, diguanidinobutanase, methylenediurea deaminase, proclavaminate amidinohydrolase, N-succinylarginine dihydrolase, N1-aminopropylagmatine ureohydrolase, Nω-hydroxy-L-arginine amidinohydrolase, and (S)-ureidoglycine aminohydrolase.

In cyclic amidines include cytosine deaminase, adenine deaminase, guanine deaminase, adenosine deaminase, cytidine deaminase, AMP deaminase, ADP deaminase, aminoimidazolase, methenyltetrahydrofolate cyclohydrolase, IMP cyclohydrolase, pterin deaminase, dCMP deaminase, dCTP deaminase, guanosine deaminase, GTP cyclohydrolase I, adenosine-phosphate deaminase, ATP deaminase, phosphoribosyl-AMP cyclohydrolase, pyrithiamine deaminase, creatinine deaminase, 1-pyrroline-4-hydroxy-2-carboxylate deaminase, blasticidin-S deaminase, sepiapterin deaminase, GTP cyclohydrolase II, diaminohydroxyphosphoribosylaminopyrimidine deaminase, methenyltetrahydromethanopterin cyclohydrolase, S-adenosylhomocysteine deaminase, GTP cyclohydrolase IIa, dCTP deaminase (dUMP-forming), S-methyl-5'-thioadenosine deaminase, 8-oxoguanine deaminase, tRNA(adenine34) deaminase, tRNAAla(adenine37) deaminase, tRNA(cytosine8) deaminase, mRNA(cytosine6666) deaminase, double-stranded RNA adenine deaminase, single-stranded DNA cytosine deaminase, GTP cyclohydrolase IV, aminodeoxyfutalosine deaminase, 5'-deoxyadenosine deaminase, N-isopropylammelide isopropylaminohydrolase, hydroxydechloroatrazine ethylaminohydrolase, ectoine hydrolase, melamine deaminase, and cAMP deaminase.

In nitriles include nitrilase, ricinine nitrilase, cyanoalanine nitrilase, arylacetonitrilase, bromoxynil nitrilase, aliphatic nitrilase, and thiocyanate hydrolase.

In other compounds include riboflavinase, aminopyrimidine aminohydrolase, 2-aminomuconate deaminase, glucosamine-6-phosphate deaminase, 1-aminocyclopropane-1-carboxylate deaminase, 5-nitroanthranilic acid aminohydrolase, 2-nitroimidazole nitrohydrolase, 2-iminobutanoate/2-iminopropanoate deaminase, and 2-aminomuconate deaminase (2-hydroxymuconate-forming).

Acting on acid anhydrides, in phosphorus-containing anhydrides include inorganic diphosphatase, trimetaphosphatase, adenosinetriphosphatase, apyrase, nucleoside diphosphate phosphatase, acylphosphatase, ATP diphosphatase, nucleotide diphosphatase, endopolyphosphatase, exopolyphosphatase, dCTP diphosphatase, ADP-ribose diphosphatase, adenosine-tetraphosphatase, nucleosidetriphosphate phosphatase, CDP-glycerol diphosphatase, bis(5'-nucleosyl)-tetraphosphatase (asymmetrical), FAD diphosphatase, 5'-acylphosphoadenosine hydrolase, ADP-sugar diphosphatase, NAD+ diphosphatase, dUTP diphosphatase, nucleoside phosphoacylhydrolase, triphosphatase, CDP-diacylglycerol diphosphatase, undecaprenyl-diphosphate phosphatase, thiamine-triphosphatase, bis(5'-adenosyl)-triphosphatase, phosphoribosyl-ATP diphosphatase, thymidine-triphosphatase, guanosine-5'-triphosphate,3'-diphosphate phosphatase, bis(5'-nucleosyl)-tetraphosphatase (symmetrical), guanosine-diphosphatase, dolichyldiphosphatase, oligosaccharide-diphosphodolichol diphosphatase, UDP-sugar diphosphatase, diphosphoinositol-polyphosphate diphosphatase, Mn2+-dependent ADP-ribose/CDP-alcohol diphosphatase, UDP-2,3-diacylglucosamine diphosphatase, 8-oxo-dGTP diphosphatase, 2-hydroxy-dATP diphosphatase, UDP-2,4-diacetamido-2,4,6-trideoxy-β-L-altropyranose hydrolase, 8-oxo-dGDP phosphatase, 5'-(N7-methyl 5'-triphosphoguanosine)-[mRNA] diphosphatase, diadenosine hexaphosphate hydrolase (AMP-forming), diadenosine hexaphosphate hydrolase (ATP-forming), 5'-(N7-methylguanosine 5'-triphospho)-[mRNA] hydrolase, α-D-ribose 1-methylphosphonate 5-triphosphate diphosphatase, inosine diphosphate phosphatase, (d)CTP diphosphatase, XTP/dITP diphosphatase, dihydroneopterin triphosphate diphosphatase, and geranyl diphosphate phosphohydrolase.

In sulfonyl-containing anhydrides include adenylylsulfatase and phosphoadenylylsulfatase.

Acting on acid anhydrides to catalyse transmembrane movement of substances include phospholipid-translocating ATPase, Mg2+-importing ATPase, Cd2+-exporting ATPase, Cu2+-exporting ATPase, Zn2+-exporting ATPase, H+-exporting ATPase, Na+-exporting ATPase, Ca2+-transporting ATPase, Na+/K+-exchanging ATPase, H+/K+-exchanging ATPase, Cl--transporting ATPase, K+-transporting ATPase, H+-transporting two-sector ATPase, Na+-transporting two-sector ATPase, arsenite-transporting ATPase, monosaccharide-transporting ATPase, oligosaccharide-transporting ATPase, maltose-transporting ATPase, glycerol-3-phosphate-transporting ATPase, polar-amino-acid-transporting ATPase, nonpolar-amino-acid-transporting ATPase, oligopeptide-transporting ATPase, nickel-transporting ATPase, sulfate-transporting ATPase, nitrate-transporting ATPase, phosphate-transporting ATPase, phosphonate-transporting ATPase, molybdate-transporting ATPase, Fe3+-transporting ATPase, polyamine-transporting ATPase, quaternary-amine-transporting ATPase, vitamin B12-transporting ATPase, iron-chelate-transporting ATPase, manganese-transporting ATPase, taurine-transporting ATPase, guanine-transporting ATPase, capsular-polysaccharide-transporting ATPase, lipopolysaccharide-transporting ATPase, teichoic-acid-transporting ATPase, heme-transporting ATPase, β-glucan-transporting ATPase, peptide-transporting ATPase, xenobiotic-transporting ATPase, cadmium-transporting ATPase, fatty-acyl-CoA-transporting ATPase, α-factor-transporting ATPase, channel-conductance-controlling ATPase, protein-secreting ATPase, mitochondrial protein-transporting ATPase, chloroplast protein-transporting ATPase, Ag+-exporting ATPase, Cu+-exporting ATPase, and tungstate-importing ATPase.

Acting on acid anhydrides to facilitate cellular and subcellular movement include myosin ATPase, dynein ATPase, microtubule-severing ATPase, plus-end-directed kinesin ATPase, minus-end-directed kinesin ATPase, vesicle-fusing ATPase, peroxisome-assembly ATPase, proteasome ATPase, chaperonin ATPase, non-chaperonin molecular chaperone ATPase, nucleoplasmin ATPase, DNA helicase, and RNA helicase.

Acting on GTP to facilitate cellular and subcellular movement include heterotrimeric G-protein GTPase, small monomeric GTPase, protein-synthesizing GTPase, signal-recognition-particle GTPase, dynamin GTPase, and tubulin GTPase.

Acting on carbon-carbon bonds, in ketonic substances include oxaloacetase, fumarylacetoacetase, kynureninase, phloretin hydrolase, acylpyruvate hydrolase, acetylpyruvate hydrolase, β-diketone hydrolase, 2,6-dioxo-6-phenylhexa-3-enoate hydrolase, 2-hydroxymuconate-6-semialdehyde hydrolase, cyclohexane-1,3-dione hydrolase,cyclohexane-1,2-dione hydrolase, cobalt-precorrin 5A hydrolase, 2-hydroxy-6-oxo-6-(2-aminophenyl)hexa-2,4-dienoate hydrolase, 2-hydroxy-6-oxonona-2,4-dienedioate hydrolase, 4,5:9,10-diseco-3-hydroxy-5,9,17-trioxoandrosta-1(10),2-diene-4-oate hydrolase, 6-oxocamphor hydrolase, 2,6-dihydroxypseudooxynicotine hydrolase, 3-fumarylpyruvate hydrolase, 6-oxocyclohex-1-ene-1-carbonyl-CoA hydratase, 3D-(3,5/4)-trihydroxycyclohexane-1,2-dione acylhydrolase (ring-opening), and maleylpyruvate hydrolase.

Acting on halide bonds, in carbon-halide compounds include alkylhalidase, (S)-2-haloacid dehalogenase, haloacetate dehalogenase, haloalkane dehalogenase, 4-chlorobenzoate dehalogenase, 4-chlorobenzoyl-CoA dehalogenase, atrazine chlorohydrolase, (R)-2-haloacid dehalogenase, 2-haloacid dehalogenase (configuration-inverting), and 2-haloacid dehalogenase (configuration-retaining).

Acting on phosphorus-nitrogen bonds include phosphoamidase, protein arginine phosphatase, and phosphohistidine phosphatase.

Acting on sulfur-nitrogen bonds include N-sulfoglucosamine sulfohydrolase and cyclamate sulfohydrolase.

Acting on carbon-phosphorus bonds include phosphonoacetaldehyde hydrolase, phosphonoacetate hydrolase, and phosphonopyruvate hydrolase.

Acting on sulfur-sulfur bonds include trithionate hydrolase.

Acting on carbon-sulfur bonds include UDP-sulfoquinovose synthase, 2'-hydroxybiphenyl-2-sulfinate desulfinase, 3-sulfinopropanoyl-CoA desulfinase, carbon disulfide hydrolase, and [CysO sulfur-carrier protein]-S-L-cysteine hydrolase.

Preferred commercially available enzymes include thiol protease (Papain from Enzybel International S.A., CAS 9001-73-4), serine endoprotease (Protamex from Novozymes), and a neutral protease that contains endopeptidase activity from *Bacillus subtilis* cultures, i.e., Metalloendopeptidase, *subtilis* neutral proteinase (Corolase® 7089 from Ab Enzymes, CAS 9001-92-7).

In one embodiment, protease mixtures may be used. Suitable protease mixtures include one or more of acid, neutral, or alkaline proteases.

Acid proteases are protein-digesting enzymes that exhibit maximum activity and stability in acid conditions (e.g., pH 2.0-5.0, 2.0-3.0, 2.0-4.0, or 3.0-5.0) and are inactivated at pH values above 6.0. Acid proteases generally have a low isoelectric point and have a low basic amino acid content.

Neutral proteases are active in a narrow pH range (pH 5 to 8) and may have relatively low thermotolerance. Neutral proteases include cysteine proteases, metalloproteases, and some of the serine proteases.

Alkaline proteases are characterized by their high activity at alkaline pH, e.g., at least pH 9, at least pH 10, at least pH 11. Examples of alkaline proteases include serine proteases. They have broad substrate specificities including esterolytic and amidase activity. The isoelectric points of serine proteases are generally between pH 4 and 6. Serine alkaline proteases that are active at highly alkaline pH represent the largest subgroup of serine proteases.

In one embodiment, the protease mixture includes proteases from *Bacillus Licheniformis*. Acid, neutral, and alkaline proteases from *Bacillus Licheniformis* are known in the art. See for example, Yilmaz et al., J Enzyme Inhib Med Chem, 2016, 31(6):1241-1247; Rao et al., Microbiology and Molecular Biology Reviews, 1998, 62(3): 597-635; and Jellouli et al., Process Biochemistry, 2011, 46(6): 1248-1256.

In one embodiment, the protease mixture includes a food grade cell wall degrading enzyme obtained from the organisms from the genus *Aspergillus*. Examples of cell wall degrading enzymes from *Aspergillus* include mylase, pectinase, xylanase, and cellulose enzymes. Specific examples include β-glucosidase, endoglucanase, filterpaperase, polygalacturonase, and pectate lyase.

In one embodiment, the method of the present invention includes addition of a first protease mixture having at least one alkaline protease; and a second protease mixture having at least one of an acid protease, a neutral protease, and an alkaline protease.

The first protease mixture includes at least one, at least two, at least three, or at least four alkaline protease. In one embodiment, the alkaline protease(s) is from *Bacillus Licheniformis*. In one embodiment, the first protease mixture includes only endoproteases.

In one embodiment, the first protease mixture includes one alkaline protease.

In one embodiment, the first protease mixture includes two alkaline proteases. In one embodiment, the first alkaline protease and second alkaline protease total 100% of the proteases of the first protease mixture. In one embodiment, the first alkaline protease is 1-80% of the protease mixture and the second alkaline protease is 1-80% of the protease mixture. In one embodiment, the first alkaline protease is 1-30% of the protease mixture and the second alkaline protease is 70-99% of the protease mixture. In one embodiment, the first alkaline protease is 1-10% of the protease mixture and the second alkaline protease is 9-99% of the protease mixture. In one embodiment, the first alkaline protease and second alkaline protease are present in equal proportions in the first protease mixture.

In one embodiment, the first protease mixture includes three alkaline proteases. In one embodiment, the first alkaline protease, second alkaline protease, and the third alkaline protease total 100% of the proteases of the first protease mixture. In one embodiment, the first alkaline protease is 1-80% of the protease mixture, the second alkaline protease is 1-80% of the protease mixture, and the third alkaline protease is 1-80% of the protease mixture. In one embodiment, the first alkaline protease is 1-30% of the protease mixture, the second alkaline protease is 1-30% of the protease mixture, and the third alkaline protease is 50-98% of the protease mixture. In one embodiment, the first alkaline protease is 1-10% of the protease mixture, second alkaline protease is 1-30% of the protease mixture, and the third alkaline protease is 10-98% of the protease mixture. In one embodiment, the first alkaline protease, second alkaline protease, and third alkaline protease are present in equal proportions in the first protease mixture.

The second protease mixture includes at least one of: acid protease, a neutral protease, and an alkaline protease. In one embodiment, the acid protease, neutral protease, or alkaline protease are from *Bacillus Licheniformis*. The proteases of the second protease mixture may include exoproteases and endoproteases.

In one embodiment, the second protease mixture includes an acid protease and a neutral protease. In one embodiment, the acid protease and neutral protease total 100% of the proteases of the second protease mixture. In one embodiment, the second protease mixture includes 1-80% acid protease and 1-80% neutral protease. In one embodiment, the acid protease is 1-30% of the protease mixture and the neutral protease is 70-99% of the protease mixture. In one embodiment, the acid protease is 1-10% of the protease mixture and neutral protease is 9-99% of the protease mixture. In one embodiment, the acid protease and neutral protease are present in equal proportions in the second protease mixture.

In one embodiment, the second protease mixture includes an acid protease and an alkaline protease. In one embodiment, the acid protease and alkaline protease total 100% of the proteases of the second protease mixture. In one embodiment, the second protease mixture includes 1-80% acid protease and 1-80% alkaline protease. In one embodiment, the acid protease is 1-30% of the protease mixture and the alkaline protease is 70-99% of the protease mixture. In one embodiment, the acid protease is 1-10% of the protease mixture and the alkaline protease is 9-99% of the protease mixture. In one embodiment, the acid protease and alkaline protease are present in equal proportions in the second protease mixture.

In one embodiment, the second protease mixture includes an neutral protease and an alkaline protease. In one embodiment, the first neutral protease and alkaline protease total 100% of the proteases of the second protease mixture. In one embodiment, the second protease mixture includes 1-80% neutral protease and 1-80% alkaline protease. In one embodiment, the neutral protease is 1-30% of the protease mixture and the alkaline protease is 70-99% of the protease mixture. In one embodiment, the neutral protease is 1-10% of the protease mixture and the alkaline protease is 9-99% of the protease mixture. In one embodiment, the neutral protease and alkaline protease are present in equal proportions in the second protease mixture.

In one embodiment, the second protease mixture includes an acid protease, a neutral protease, and an alkaline protease. In one embodiment, the acid protease, neutral protease, and alkaline protease total 100% of the proteases of the second protease mixture. In one embodiment, the second protease mixture contains 1-80% acid protease, 1-80% neutral protease, and 1-80% alkaline protease. In one embodiment, the second protease mixture contains 1-10% acid protease, 1-30% neutral protease, and 60-98% alkaline protease. In one embodiment, the acid protease, neutral protease, and alkaline protease are present in equal proportions in the second protease mixture.

In one embodiment, the alkaline protease of the first protease mixture is not in the second protease mixture.

In one embodiment, the amount of first protease mixture/ second protease mixture is 0.2-0.6% first protease mixture and 0.02-0.06% of the second protease mixture. In one embodiment, the amount of first protease mixture/second protease mixture is 0.3-0.5% first protease mixture and 0.03-0.05% of the second protease mixture. In one embodiment, the amount of first protease mixture is about 0.4% and the amount of second is about 0.04%.

A preferred commercially available protease mixture for the first protease mixture includes Endocut-02L (TailorFood/ Tailorzyme). Endocut-02L is comprised of an endoprotease mixture, also referred to herein as Endocut protease mixture. A preferred commercially available protease mixture for the second protease mixture includes Exocut-BL (TailorFood/ Tailorzyme). Exocut-BL is comprised of an exoprotease mixture, also referred to herein as Exocut protease mixture. Exocut-BL may include a cell wall degrading enzyme from *Aspergillus*, instead of or in addition to one or more protease.

The following values may be combined in any manner to create a range with a minima and maxima for the quantity of Endocut protease mixture as a percentage of the total weight of the disintegrated crustacean catch: 0.01%, 0.1%, 0.2%, 0.3%, 0.4%, 0.5%, 0.6%, 0.7%, 0.8%, 0.9%, 1.0%, or 1.5%.

The following values may be combined in any manner to create a range with a minima and maxima for the quantity of Exocut protease mixture as a percentage of the total weight of the disintegrated crustacean catch: 0.005%, 0.01%, 0.02%, 0.03%, 0.04%, 0.05%, 0.06%, 0.07%, 0.08%, 0.09%, 0.1%, 0.25%, or 0.5%.

In one embodiment, the amount of Endocut/Exocut is 0.2-0.6% Endocut protease mixture and 0.02-0.06% of the Exocut protease mixture. In one embodiment, the amount of Endocut/Exocut is 0.3-0.5% Endocut protease mixture and 0.03-0.05% of the Exocut protease mixture. In one embodiment, the amount of Endocut is about 0.4% and the amount of Exocut is about 0.04%.

In one embodiment, the first protease mixture and second protease mixture are simultaneously added to the disintegrated crustacean catch.

In one embodiment, the hydrolysis step includes contacting the crustacean catch with the first protease mixture prior to contacting the crustacean catch with the second protease mixture. In this embodiment, the following values in minutes may be combined in any manner to create a range with a minima and maxima for time necessary for hydrolysis with the first protease mixture, prior to the addition of the second protease mixture: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, and 240. For example, the disintegrated crustacean catch is hydrolyzed for 1-10 minutes with the first protease mixture prior to the addition of the second protease mixture.

In one embodiment, the hydrolysis step includes contacting the second protease mixture with the disintegrated crustacean catch prior to contacting the crustacean catch with the first protease mixture. In this embodiment, the following values in minutes may be combined in any manner to create a range with a minima and maxima for time necessary for hydrolysis with the second protease mixture, prior to the addition of the first protease mixture: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, and 240. For example, the disintegrated crustacean catch is hydrolyzed for 1-10 minutes with the second protease mixture prior to the addition of the first protease mixture. In another embodiment, a second enzyme comprising chitinase or collagenase is used. This enzyme may be used in combination with a first enzyme or enzyme combination.

In another embodiment, the enzyme(s) used in hydrolysis do not contain an exopeptidase.

The contacting step may also include the use of an organic solvent. Examples of useful organic solvents include, but are not limited to, ethanol, acetone, and ethylacetate.

Stopping Hydrolysis

Hydrolysis may be stopped by inactivating the enzyme(s). The enzyme(s) may be deactivated in different ways including adding inhibitors, removing co-factors (e.g. crucial ions through dialysis), through thermal inactivation, and/or by any other deactivating means.

Conditions whereby each enzyme is inactivated may vary, but normally include raising the pH and temperature of the solution. For example, deactivation of Corolase® 7089 begins at pH values >7.5 and temperatures greater than 55° C. The conditions are chosen so that the enzyme is inactivated at temperatures that will not denature the protein from the disintegrated crustacean catch. The following temperatures may be combined in any manner to create a minima, a maxima, or a range for the temperatures under which the enzyme(s) is inactivated without denaturing the protein from the crustacean catch: 85° C., 86° C., 87° C., 88° C., 89° C., 90° C., 91° C., 92° C., 93° C., 94° C., 95° C., 96° C., 97° C., 98° C., 99° C., and 100° C. For example, enzyme A may be inactivated at a temperature over about 90° C. or preferably between about 92° C. and about 98° C.

As discussed above, hydrolysis is stopped at the correct moment so that the crustacean catch is preferably only partially hydrolyzed to produce a hydrolyzed crustacean catch wherein the proteins have a specified degree of hydrolysis. Furthermore, a person having ordinary skill in the art would be able to ascertain the conditions and duration of hydrolysis with specific enzyme(s) and conditions to produce a hydrolyzed crustacean catch wherein a certain percentage of the crustacean catch is hydrolyzed.

Separating to Provide Protein Phospholipid Complex

The third step involves separating the hydrolyzed crustacean catch to provide a PPC. During this step, various processes may be utilized to ensure that the PPC meets certain criteria. For example, the lipid content of the PPC is approximately 30-55%. In another example, fluoride levels may be reduced to produce a PPC with a fluoride content of less than about 5 mg per kg of PPC.

Reducing fluoride content can be effectuated in various manners. For example, the exoskeletons, i.e., crust, carapace, and/or shell, of the crustacean catch are usually high in fluoride. Removing the exoskeletons, e.g., shells, from the hydrolyzed crustacean catch is one way to lower fluoride content. The shells may be removed by various means such as with a filter, sieve, decanter, or centrifuge. For example, the size of the openings for a filter or sieve may be chosen so that all or the majority of the shells are removed without removing much of or any of the non-shell hydrolysis products. A standard woven wire sieve may be used with mesh sizes selected from about 125 mm, 25 mm, 4 mm, 1 mm, 250 µm, 45 µm, and 20 µm. U.S. Pat. Nos. 8,557,297 and 9,068,142 to Bruheim, et al., which disclose methods of reducing fluoride content from crustacean material, are hereby incorporated by reference in their entirety.

The shells may also be removed at various points during the process. For example, the shells may be removed by decanter or sieve immediately after hydrolysis but prior to pasteurization and inactivation of the enzyme(s).

Reducing the fluorine content may also be accomplished downstream when the krill oil is produced by supercritical extraction and/or subcritical fluid extraction. Therefore, the shells may be removed after hydrolyzation from the main process line and reintroduced to the main process line after the enzyme inactivation process. In other words, the shells and/or any other insoluble particle may be reintroduced into the main process line before drying. Reintroducing the shells and/or any other insoluble particle into the main process line may be beneficial for utility of the PPC because the shells allow the product to be packed into firm blocks which are easier to break apart and allow for greater flowability in downstream processing steps. The insoluble particle is preferably food grade and may be easily removed from the PPC downstream. Examples of insoluble particles include fibers.

Alternatively, the shells do not have to be removed at any time during the process and may be part of the PPC. As mentioned above, any excess fluorine associated with the shells may be removed downstream by supercritical processing.

In another example, water levels may be reduced to prevent microbiological activity during the separating step. The water content of the PPC is the percentage of water whereby microbial growth is less likely. The following percentages can be used to create a minima, a maxima, or a range of values for the water content of the PPC: 1%, 2%, 3%, 4%, 5%, 6%, 7%, 8%, 9%, 10%, 11%, 12%, 13%, 14%, or 15% w/w. For example, the PPC contains less than about 15% water based upon the total weight of the PPC. Ideally the water activity is less than about 0.85 and preferably about 0.65.

Water can be removed after hydrolysis by more than one dewatering step which may include drying and mechanical removal before, during, or after the separation process. Preferred dewatering methods include low temperature drying under vacuum and processing with a decanter centrifuge for soft sediment or a horizontal centrifuge. Any method of separation may be used such as a decanter and a separator. The preferred separators use rotational forces to spin the sample to separate the sample into layers.

A horizontal centrifuge is any device that is capable of rotating a mixture in the Z-plane, as opposed to the X-plane and/or Y-plane as with conventional centrifuges. The rotation is generated by a screw-type conveyor element aligned horizontally within a tube shaped enclosure. The induced centrifugal force then layers the heavier particles to the outside edges of the enclosure, while the lighter particles form layers closer to the center of the enclosure. Some horizontal centrifuges are modifies to comprise an extended separation pathway and induce high gravitational forces. A preferred horizontal centrifuge is a Flottweg Sedicanter® which mechanically separates water from the sediment. The Sedicanter® is a modified horizontal centrifuge including a long horizontal clarification/separation zone and generates high centrifugal forces (5,000 to 10,000 g). The Sedicanter® S3E-3 model has a 12" bowl diameter, bowl rotation speed of 7750 rpm, dimensions of 90"×28"×30", and a weight of 2315 lbs.

Protein Phospholipid Emulsion

Another aspect of the invention relates to a method of producing a stable protein phospholipid emulsion. In this method, particular enzymes and processing parameters are selected to ensure the end product is a stable emulsion. A stable emulsion is desired to protect functional ingredients such as the phospholipids, fatty acids, and hydrolyzed proteins and to improve handling, stability, and efficacy of these functional ingredients.

A stable emulsion is defined as an emulsion that does not separate at room temperature or slightly elevated temperatures as determined upon visional inspection and/or viscosity measurements. The following temperatures may represent a minima or a maxima or may be combined to create a range of temperatures used to define the elevated temperatures: 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., and 45° C. The following time periods in months may represent a minima or a maxima or may be combined to create a range used to define the requirements of how long an emulsion must remain stable at an elevated temperature as described above: 3, 4, 5, 6, 7, 8, 9, 10, 11, 12, 13, 14, 15, 16, 17, 18, 19, 20, 21, 22, 23, or 24 months. For example, a stable emulsion may be defined as an emulsion that does not separate at a temperature up to about 40° C. for 4 months or, in another example, ambient temperature (e.g., between 20° C. and 25° C.) for 6 months. Additionally, a stable emulsion contains a water content ideal to prevent microbiological growth and fall within safety guidelines for human consumption.

The crustacean catch is disintegrated in the first step as described above. In the second step, the disintegrated crustacean catch is contacted with a proteolytic enzyme to provide a hydrolyzed crustacean catch. In this step, the choice of enzyme(s) is critical to ensure that the enzyme(s) do not inhibit the phospholipids from forming stable emulsions. The parameters for the contacting step are as described above.

In the third step, the hydrolyzed crustacean catch is separated to provide a stable phospholipid emulsion. This third step may include a fluid extraction process such as supercritical processing.

The water content of the stable protein phospholipid emulsion may be any of the following values which represent an individual minima and maxima or can be combined to create a range: 40% v/v, 41% v/v, 42% v/v, 43% v/v, 44% v/v, 45% v/v, 46% v/v, 47% v/v, 48% v/v, 49% v/v, 50% v/v, 51% v/v, 52% v/v, 53% v/v, 54% v/v, 55% v/v, 56% v/v, 57% v/v, 58% v/v, 59% v/v, and 60% v/v. For example, the preferred water content is about 45-55% v/v.

Another aspect of the invention relates to a stable protein phospholipid emulsion including water, protein, and lipid.

Crustacean Oil

Another aspect of the invention relates to a method of producing crustacean oil. The method includes the steps of disintegrating a crustacean catch to provide a disintegrated crustacean catch comprising protein; contacting the disintegrated crustacean catch with one or more proteolytic enzymes to provide a hydrolyzed crustacean catch without substantially denaturing the protein; and separating the hydrolyzed crustacean catch to provide a PPC. These steps are as described above. The method also includes a fourth step which involves extracting crustacean oil from the PPC.

The extraction step preferably involves using fluid extraction to separate the oil from the PPC. Preferred fluids include supercritical $CO_2$, ethanol, acetone, and/or a $C_1$-$C_3$ monohydric alcohol. Supercritical $CO_2$ refers to any mixture comprising $CO_2$ in a fluid state while held at, or above, its critical temperature and critical pressure where its characteristics expand to fill a container like a gas but with a density like that of a liquid. Carbon dioxide becomes supercritical above 31.1° C. and 72.9 atm/7.39 MPa.

Some methods of extracting the crustacean oil from the PPC are described in U.S. Pat. No. 9,034,388 to Bruheim, et al., the content of which is incorporated by reference in its entirety. Supercritical processing is also discussed in U.S. Pat. No. 9,068,142 to Bruheim, et al., the content of which is incorporated by reference in its entirety.

For example, crustacean oil may be extracted from the PPC using a two stage process. In stage 1, the neutral lipid is removed by extracting with a neat supercritical $CO_2$ or $CO_2$ plus approximately 1-10% of a co-solvent (e.g., ethanol). In stage 2, the crustacean oil is extracted using supercritical $CO_2$ in combination with approximately 10-30% ethanol.

The preferred crustacean oil is krill oil and the disintegrated crustacean catch is preferably disintegrated hill.

The crustacean oil preferably contains about 400-500 g/Kg phospholipids and approximately 200-260 g/Kg Omega-3 fatty acids.

One or more other nutritional oils may be combined with the crustacean oil of the invention to create a single dosage form with health benefits. The nutritional oils may be derived from other marine sources, plant sources, or other animal sources. Some examples of nutritional oils include, but are not limited to, vegetable oil (such as flaxseed oil, pumpkinseed oil, canola oil, soybean oil, or walnut oil), fish oil, seal oil, microalgae oil, mussels oil, and shrimp oil. A preferred additional marine source is green-lipped mussel oil.

The crustacean oils discussed above are suitable for administration to humans and animals, such as dogs, for various health benefits. For example, pets such as dogs have been administered hill oil capsules directly or krill oil is placed directly on their food.

Another aspect of the invention relates to a method of producing crustacean oil without an extraction step, i.e., in the absence of an extraction step. The method includes the steps of disintegrating a crustacean catch to provide a disintegrated crustacean catch comprising protein; contacting the disintegrated crustacean catch with a proteolytic enzyme to provide a hydrolyzed crustacean catch without substantially denaturing the protein; and separating the hydrolyzed crustacean catch to provide a free crustacean oil. The preferred proteolytic enzymes would be those that can provide a nearly complete hydrolysis that releases the crustacean oil as a free oil. For example, the preferred proteolytic enzymes are a mixture of acid, neutral, and alkaline proteases from *Bacillus Licheniformis*.

Reference throughout this specification to "one embodiment," "an embodiment," "one example," or "an example" means that a particular feature, structure or characteristic described in connection with the embodiment or example is included in at least one embodiment of the present embodiments. Thus, appearances of the phrases "in one embodiment," "in an embodiment," "one example," or "an example" in various places throughout this specification are not necessarily all referring to the same embodiment or example. Furthermore, the particular features, structures, or characteristics may be combined in any suitable combinations and/or sub-combinations in one or more embodiments or examples. In addition, it is appreciated that the figures provided herewith are for explanation purposes to persons ordinarily skilled in the art.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

EXAMPLES

Example 1

Within 30 minutes of being caught, fresh krill is shredded using a knife cutter to roughly particles of 3-6 mm in size. The temperature of the krill is roughly 1-2° C. at this time. A mixture of fresh water (up to 50% w/w by the weight of the hill) and enzyme (about 0.2% w/w of the weight of the krill) is added and heated to a temperature of about 50° C. Hyrdolysis takes roughly 30 minutes. The amount of enzyme, temperature, and duration of hydrolysis are critically chosen to ensure that the krill protein is not denatured during hydrolysis.

After hydrolysis, the shells are separated from the main process line with a sieve or a decanter. Then the hydrolyzed krill in the main process line is pasteurized to ensure hygienic quality and to inactivate the enzymes. Pasteurization takes place at 90° C. for a minimum of 10 minutes. The hydrolyzed hill is subsequently dried using a sedicanter to mechanically separate excess water and low temperature vacuum drying. The resulting product is the PPC.

Example 2

Krill is processed as outlined in Example 1 except that the decanter step following hydrolysis is removed. After hydrolysis, the hill bypasses the decanter. Therefore, the krill shells remain within the hydrolyzed hill and proceeds down the main process line to pasteurization and then the sedicanter and low temperature vacuum drying.

Accordingly, the krill shells remain mixed with the PPC. Having the krill shell mixed with the product is beneficial because the shells allow the firm product blocks to be easily broken up and increase flowability during processing. Another benefit is that any small protein fraction still connected to the shells after hydrolyzation is still kept with the product instead of being separated out with the shells.

Excess fluoride within the product due to the presence of the shells may be removed downstream during supercritical extraction.

Example 3

After the krill is hydrolyzed, the hill shells are separated from the main process line. However, the shells are reintroduced to the main process line after bypassing the inactivation process and the sedicanter, i.e., before the dryer.

Thus, while there have been described the preferred embodiments of the present invention, those skilled in the art will realize that other embodiments can be made without departing from the spirit of the invention, which includes all such further modifications and changes as come within the true scope of the claims set forth herein.

Example 4

500 kg hill (minced to 5 mm) is added to 500 kg water. Endocut/Exocut from Tailorzymes is added at a dose of 0.4% and 0.04%, respectively. The reaction is run at 55° C. for 2 hours. The decanter is run at 5400 rpm with a flow rate of 800 ltr/hr. The separator is run at about 8200 rpm, flow rate of 1000 ltr/hr and shooting at every 300 seconds. The shooting time refers to the time for release of the hydrolysate.

TABLE 1

Mass balance from Example 4.

| Products | Mass (kg) | Mass (%) | Dry matter (%) | Yield (%) |
|---|---|---|---|---|
| Shells | 55 | 5.7 | 30 | 3.44 |
| Hydrolysate | 700 | 73 | 9.5 | 13.85 |
| PPC | 160 | 16.7 | 25 | 8.33 |
| Loss | 45 | 4.6 | | |

Example 5

500 kg hill is added to 500 kg water. Endocut/Exocut is added at a dose of 0.4% and 0.04%, respectively. The reaction temperature is 55° C. and reaction time is 2 hours.

The decanter is run at 5400 rpm, flow 800 ltr/hr. Temperature increased to 90 degrees and the hydrolysate was processed over the separator, which ran at 8200 rpm, flow 1000 ltr/hr. The shooting of the hydrolysate was increased stepwise to shooting at every 900 seconds.

TABLE 2

Mass balance from example 5.

| Products | Mass (kg) | Mass (%) | Dry matter (%) | Yield (%) |
|---|---|---|---|---|
| Shells | 40 | 4.2 | 30 | 2.5 |
| Hydrolysate | 750 | 78 | 9.5 | 14.84 |
| PPC | 120 | 12.5 | 25 | 6.25 |
| Loss | 50 | 5.3 | | |

Example 6

300 kg hill is added to 300 kg water and Corrolase 7089 (at a dose of 0.15%). The reaction is run at a temperature of 55° C. for a total reaction time of 1 hour before entering the decanter (Shell removal), followed by another 2 hours before inactivation.

The decanter ran at 2800 rpm, flow 650 ltr/hr. The separator was running at about 8200 rpm, flow 1000 ltr/hr and shooting at every 300 seconds. No free oil formed.

TABLE 3

Mass balance from example 6.

| Products | Mass (kg) | Mass (%) | Dry matter (%) | Yield (%) |
|---|---|---|---|---|
| Shells | 43 | 7.17 | 28 | 4.3 |
| Hydrolysate | 409 | 68.17 | 9.5 | 12.95 |
| PPC | 105 | 17.50 | 25 | 8.75 |
| Loss | 43 | 7.17 | | |

Example 7

220 kg hill is mixed with 55 kg water and Corrolase 7089 (at a dose of 0.15%). The reaction takes place at a temperature of 55° C. and the reaction time is 1 hour before decanting, followed by another 2 hours before inactivation.

The decanter ran at 2800 rpm, flow 650 ltr/hr. The separator was running at about 8200 rpm, flow 1000 ltr/hr and shooting at every 300 seconds. No free oil formed.

TABLE 4

Mass balance from example 7.

| Products | Mass (kg) | Mass (%) | Dry matter (%) | Yield (%) |
|---|---|---|---|---|
| Shells | 26 | 9.45 | 32 | 3.78 |
| Hydrolysate | 178 | 64.73 | 14 | 11.33 |
| PPC | 55 | 20 | 25 | 6.25 |
| Loss | 16 | 5.82 | | |

Example 8

500 kg hill is mixed with 125 kg water and Endocut/Exocut (at a dose of 0.4% and 0.04%, respectively). The reaction temperature is 55° C. The reaction runs for 1 hour before decanting, followed by 30 minutes before inactivation. Decanter: 2800 rpm, flow 650 ltr/hr.

TABLE 5

Mass balance from example 8.

| Products | Mass (kg) | Mass (%) | Dry matter (%) | Yield (%) |
|---|---|---|---|---|
| Shells | 50 | 8 | 32 | 3.2 |
| Hydrolysate | 517 | 87.2 | 14 | 14.48 |
| PPC | 33 | 5.28 | 25 | 1.65 |
| Loss | 25 | 4 | | |

The separator was running at about 8200 rpm, flow 1000 ltr/hr and shooting at every 600 seconds.

After some changes in the settings (i.e. counterpressure) it was possible to separate free oil from the separator. The oil had the following composition (Table 6).

TABLE 6

Composition of free oil formed during example 8.

| Parameter | Amount |
|---|---|
| Crude Protein (N = 6.25) | 74 g/kg |
| Crude fat | 443 g/kg |
| Crude Ash (550° C.) | 40 g/kg |
| Fluoride | 411 mg/kg |
| Phosphatidylcholine | 93.7 g/kg |
| Lyso-Phosphatidylcholine | 13.5 g/kg |
| Phosphatidylethanolamine | 4.2 g/kg |
| N-acyl-Phosphatidylethanolamine | 0.5 g/kg |
| Lyso-Phosphatidylethanolamine | 1 g/kg |
| Watercontent (Karl Fischer) | 400 g/kg |
| Astaxanthine | 7.1 mg/kg |

Example 9

Hydrolysate from Example 4 was then processed further by micro and nano-filtration to remove molecules with less than 300-400 Dalton.

Hydrolysate with 50% DM was diluted with water to a brix value of 8.

Retentate was dried using spray drying.

Dried product was used to mix with beverage and the result was a taste and smell free drink.

Example 10

The enzymatic hydrolysis was performed in a Distek Premiere 5100 Dissolution System at 55° C. and 150 RPM. Enzyme dosing of Endocut-02L was varied from 1 kg/ton to 5 kg/ton based, whilst enzyme dosing of Exocut-BL was varied from 0.05 kg/ton to 0.4 kg/ton, both additions based on raw material. The raw material was processed in a meat-grinder using a 4.5 mm grinder plate and water added in accordance with the table below, all prior to enzyme addition. After a total reaction time of either 60 or 120 minutes, inactivation was conducted by means of heating (95° C.), followed by initial separation of the shells by sieve, and subsequently filtration of the remaining suspension. For some trials, final inactivation was conducted after separation of the shells. All fractions were retained and weighted for mass balance calculation and post analysis.

TABLE 7

Experimental setup

| | | Reaction Conditions | | | | | |
|---|---|---|---|---|---|---|---|
| ID | Description | Endocut-02L [g/kg] | Exocut-BL [g/kg] | Temp. [° C.] | Stirring speed [rpm] | Reaction time [min] | Water addition [%] | Inactivation |
| 0 | Blind | 0 | 0 | 55 | 150 | 120 | 100% | 95° C. incl. shells |
| 1 | Endocut-02L + BL | 1 | 0 | 55 | 150 | 120 | 25% | 95° C. incl. shells |
| 2 | Endocut-02L + BL | 4 | 0.4 | 55 | 150 | 120 | 100% | 95° C. incl. shells |
| 3 | Endocut-02L + BL | 2 | 0.2 | 55 | 150 | 120 | 100% | 95° C. incl. shells |
| 4 | Endocut-02L + BL | 1 | 0.1 | 55 | 150 | 120 | 100% | 95° C. incl. shells |
| 5 | Endocut-02L + BL | 1 | 0.05 | 55 | 150 | 120 | 100% | 95° C. incl. shells |
| 6 | Endocut-02L | 4 | 0 | 55 | 150 | 60 | 100% | 95° C. excl. shells |
| 7 | Endocut-02L + BL | 4 | 0.4 | 55 | 150 | 60 | 100% | 95° C. incl. shells |
| 8 | Endocut-02L + BL | 4 | 0.4 | 55 | 150 | 60 | 100% | 95° C. excl. shells |
| 9 | Endocut-02L | 5 | 0 | 55 | 150 | 60 | 100% | 95° C. excl. shells |
| 10 | Endocut-02L + BL | 3 | 0.3 | 55 | 150 | 60 | 100% | 95° C. excl. shells |

TABLE 8

Sensorial evaluation of hydrolysate

| | | Reaction conditions | | | | | Taste | | |
|---|---|---|---|---|---|---|---|---|---|
| ID | Description | Endocut-02L [g/kg] | Exocut-BL [g/kg] | Reaction time [min] | Water addition [%] | Inactivation | Sweetness | Bitterness | Total impression |
| 6 | Endocut-02L | 4 | 0 | 60 | 100% | 95° C. excl. Shells | • | • | ++ |
| 7 | Endocut-02L + BL | 4 | 0.4 | 60 | 100% | 95° C. incl. Shells | ••• | • | +++ |
| 8 | Endocut-02L + BL | 4 | 0.4 | 60 | 100% | 95° C. excl. Shells | •• | • | +++ |
| 9 | Endocut-02L | 5 | 0 | 60 | 100% | 95° C. excl. Shells | • | ••• | + |
| 10 | Endocut-02L + BL | 3 | 0.3 | 60 | 100% | 95° C. excl. Shells | •• | • | ++ |

The invention claimed is:

1. A method of producing polar krill oil comprising the steps of
   a) disintegrating a krill catch to provide a disintegrated krill catch;
   b) contacting the disintegrated krill catch with about 0.1-0.5% endoprotease mixture and about 0.01-0.05% exoprotease mixture by total weight of the disintegrated krill catch to provide a hydrolyzed krill catch; and
   separating the hydrolyzed krill catch to provide a polar krill oil.

2. The method according to claim 1, wherein the method is performed in the absence of an additional extraction step.

3. The method according to claim 1, wherein the hydrolyzed krill catch is separated in step (c) with a filter, sieve, decanter, centrifuge, or a combination thereof.

4. The method according to claim 3, wherein the hydrolyzed krill catch is separated in step (c) with a horizontal centrifuge.

5. The method according to claim 1, wherein the ratio of endoprotease mixture to exoprotease mixture is about 10:1.

6. The method according to claim 1, wherein the contacting of step (b) includes contacting with a cell wall degrading enzyme.

7. The method according to claim 6, wherein the cell wall degrading enzyme is from the genus *Aspergillus*.

8. The method according to claim 7, wherein the cell wall degrading enzyme is mylase, pectinase, xylanase, cellulose enzymes, or a combination thereof.

9. The method according to claim 1, wherein the disintegrated krill catch is contacted with the enzymes for over 100 minutes to provide a hydrolyzed krill catch.

10. The method according to claim 1, wherein said disintegrating comprises one or more of pulping, milling, grinding or shredding.

11. The method acccording to claim 1, wherein said contacting comprises an organic solvent.

12. The method according to claim 1, wherein said contacting comprises incubating the disintegrated krill catch at a temperature range of 45-75° C.

* * * * *